US008652083B2

(12) United States Patent
Weitzner et al.

(10) Patent No.: US 8,652,083 B2
(45) Date of Patent: *Feb. 18, 2014

(54) ANTI-OBESITY STENT

(75) Inventors: Barry Weitzner, Acton, MA (US);
Taryn Deneault, Worcester, MA (US);
Katie Krueger, Merrimack, NH (US);
Claude Clerc, Marlboro, MA (US);
Harold M. Martins, Newton, MA (US);
William Bertolino, Framingham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 379 days.

This patent is subject to a terminal disclaimer.

(21) Appl. No.: 13/179,197

(22) Filed: Jul. 8, 2011

(65) Prior Publication Data

US 2011/0270406 A1 Nov. 3, 2011

Related U.S. Application Data

(63) Continuation of application No. 11/443,537, filed on May 30, 2006, now Pat. No. 8,002,731.

(51) Int. Cl.
*A61M 5/00* (2006.01)
*A61F 2/04* (2013.01)

(52) U.S. Cl.
USPC .............................. 604/8; 623/23.65; 623/23.7

(58) Field of Classification Search
USPC ............. 604/8–10, 19, 27, 28, 48, 500, 604/506–508, 523, 533; 606/1, 8, 108, 606/139–140, 151, 153–159, 191, 201, 606/203; 623/23.64–23.68, 23.7; 600/37

See application file for complete search history.

(56) References Cited

U.S. PATENT DOCUMENTS

| 7,227,237 B2 * | 6/2007 | Lu et al. ......................... 257/458 |
| 8,002,731 B2 * | 8/2011 | Weitzner et al. .................. 604/8 |
| 2005/0043817 A1 * | 2/2005 | McKenna et al. .......... 623/23.65 |

FOREIGN PATENT DOCUMENTS

| JP | 2005 500 127 | 1/2005 |
| JP | 2005 066 341 | 3/2005 |
| JP | 2005 522 269 | 7/2005 |
| JP | 2006 507 910 | 3/2006 |
| WO | 2005/060882 | 7/2005 |

* cited by examiner

*Primary Examiner* — Philip R Wiest
(74) *Attorney, Agent, or Firm* — Fay Kaplun & Marcin, LLP

(57) ABSTRACT

The anti-obesity stent includes a tubular structure having outer and inner surfaces and proximal and distal ends. The tubular structure is sized to fit within a duodenum in substantially coaxial relation therewith. The tubular structure is impervious or semi-permeable to digestive substances and chyme within the duodenum. The anti-obesity stent includes a transport structure at least a part of which is coincident with or connected to the outer surface. The transport structure extends to the distal end of the tubular structure. At least one retainer structure is connected to the tubular structure. The retainer structure secures the tubular structure within the duodenum such that the transport structure is positioned to receive digestive fluids from a papilla of Vater on an inner surface of the duodenum. The transport structure provides a conduit for the digestive fluids therein to flow to the distal end.

20 Claims, 12 Drawing Sheets

ANTI-OBESITY STENT

CROSS-REFERENCE TO RELATED APPLICATION

This application is a continuation of U.S. application Ser. No. 11/443,537, filed May 30, 2006, the entire contents of which are incorporated herein by reference.

FIELD OF THE INVENTION

The present invention relates generally to anti-obesity stents and methods for using the same, and more specifically, to anti-obesity stents which are secured in the duodenum adjacent to the stomach to reduce digestion and absorption of food.

BACKGROUND OF THE INVENTION

The incidence of obesity and its associated health-related problems has become significant. The causes of obesity may involve a complex interplay of genetic, environmental, psycho-behavioral, endocrine, metabolic, cultural, and socio-economic factors. Severe obesity is frequently associated with significant comorbid medical conditions, including coronary artery disease, hypertension, type II diabetes mellitus, gallstones, nonalcoholic steatohepatitis, pulmonary hypertension, and sleep apnea. Obesity is a leading cause of preventable death in the U.S. The spectrum of comorbid conditions associated with obesity includes cancer, osteoarthritis, and heart disease. The economic cost of obesity is substantial.

Current treatments for obesity range from diet, exercise, behavioral modification, and pharmacotherapy to various types of surgery, with varying risks and efficacy. In general, nonsurgical treatments, although less invasive, achieve only relatively short-term and limited weight loss in most patients. Non-surgical treatments are utilized for patients such as with a body-mass index (BMI) which is greater than 30, and have not proven very effective. Surgical treatments include gastroplasty to restrict the capacity of the stomach to hold large amounts of food, such as by stapling or "gastric banding". Other surgical procedures include gastric bypass and gastric "balloons" which, when deflated, may be inserted into the stomach and then are distended by filling with saline solution.

Surgical interventions may be performed on those patients with a BMI which is greater than 40 (deemed morbidly obese). Surgical interventions may include restrictive operations that reduce the size of the stomach pouch to limit food intake. Surgical interventions may also include malabsorptive procedures that rearrange the small intestine in an attempt to decrease the functional length or efficiency of nutrient absorption, or a combination thereof. One combination procedure is Gastric Bypass (GPB or Roux-en-Y) which has been effective for most patients who maintain about 70% of excess weight loss after 5 years, and 50% thereof after 10 years. Both of these types of procedures may be performed laparoscopically, but may have complications. Also, GPB is normally irreversible. Other treatment approaches are being considered. Excess weight loss is the loss of weight which is greater than the ideal body weight.

The need exists for low cost, less invasive interventions for the treatment of obesity, including morbid obesity.

SUMMARY OF THE INVENTION

The anti-obesity stent of the present invention includes a tubular structure having outer and inner surfaces and proximal and distal ends. The tubular structure is sized to fit within a duodenum in substantially coaxial relation therewith. The tubular structure is impervious or semi-permeable to digestive substances and chyme within the duodenum. Chyme is the partially digested food which flows into the duodenum from the stomach. The anti-obesity stent includes a transport structure at least a part of which is coincident with or connected to the outer surface. The transport structure extends to the distal end of the tubular structure. At least one retainer structure is connected to the tubular structure. The retainer structure secures the tubular structure within the duodenum such that the transport structure is positioned to receive digestive fluids from a papilla of Vater on an inner surface of the duodenum. The transport structure provides a conduit for the digestive fluids therein to flow to the distal end.

The anti-obesity stent, when secured in the proper location within the duodenum, reduces or prevents mixing of the chyme and digestive substances within the duodenum. The digestive substances within the duodenum include digestive fluids, such as biliary and pancreatic juices, which reach the interior of the duodenum by flowing through the papilla of Vater which is contiguous with the inner surface of the duodenum. The digestive fluids are supplied to the papilla of Vater by the bile and pancreatic ducts. The anti-obesity stent reduces or prevents mixing of the chyme and digestive fluids by reducing or preventing the digestive fluids which flow through the papilla of Vater from passing through the tubular structure. Consequently, mixing of the digestive fluids with the chyme in the region of the duodenum which is occupied by the anti-obesity stent is reduced or prevented. This reduces the exposure of the chyme to the digestive fluids which reduces the associated chemical breakdown thereof. This is a result of the tubular structure being semi-permeable or impervious to the chyme. The reduction in the mixing of the chyme and digestive fluids provided by the anti-obesity stent reduces the caloric intake by the patient. Also, this reduction in the mixing reduces the breakdown of fats because the bile is separated from the chyme over the axial length of the anti-obesity stent. Consequently, the chemical transformation of the chyme by the digestive fluids which is normally required for absorption of the nutrients, fats and other substances in the chyme by the duodenum is reduced.

The anti-obesity stent reduces the absorption of fats by the small intestine, which includes the duodenum, by the following mechanisms: (i) the anti-obesity stent separates the chyme from the bile which is secreted by the papilla of Vater over the axial length of the stent; (ii) the anti-obesity stent separates the chyme from the absorptive surfaces of the small intestine which reduces the absorption of the nutrients, fats and other substances in the chyme by the small intestine; and (iii) the bile which is located between the anti-obesity stent and the absorptive surfaces of the small intestine is reabsorbed by the absorptive surface over the axial length of the stent which further reduces the availability of the bile exiting at the distal end of the stent to breakdown fats in the chyme.

The reduction in the mixing of the chyme and bile, and the separation of the chyme from the absorptive surfaces of the duodenum provided by the anti-obesity stent may significantly reduce the breakdown and absorption of fat in the chyme. Such a significant reduction may result from the absorption of fat possibly being required in the duodenum to be effective.

Additionally, the anti-obesity stent reduces the absorption of the nutrients, fats and other substances in the chyme by the duodenum. This reduced absorption results from the tubular structure being semi-permeable or impervious to the chyme. As a result, the chyme which is contained within the tubular structure is partially or completely prevented from reaching the inner surface of the portion of the duodenum in which the anti-obesity stent is located. Consequently, the portion of the duodenum in which the anti-obesity stent is located is partially or completely prevented from absorbing the nutrients, fats and other substances in the chyme. Reducing the absorption of the nutrients, fats and other substances by the duodenum reduces the caloric intake by the patient. Also, reducing the absorption of the nutrients, fats and other substances reduces the fat intake by the patient which typically reduces the weight thereof.

The anti-obesity stent does not obstruct the passage and flow of the digestive fluids through the papilla of Vater. This allows flow of the digestive fluids through the papilla of Vater into the anti-obesity stent. The anti-obesity stent further provides for the digestive fluids to be conveyed through the transport structure to the distal end of the tubular structure. The passage or flow of the digestive fluids through the papilla of Vater which is not obstructed by the anti-obesity stent is beneficial because obstruction of such passage or flow through the papilla of Vater may be undesirable.

The anti-obesity stent separates the food and chyme, which flows from the stomach into the duodenum, from the digestive fluids which include bile acids and pancreatic enzymes and which promote lipid absorption. This separation by the anti-obesity stent is provided at the location thereof in the duodenum which is the beginning of the small intestine. The anti-obesity stent treats obesity using a mal-absorptive method. Separating the food from the digestive fluids may reduce the amount of digestion and, consequently, the amount of weight a person gains from eating a specific quantity of food. Also, such separation reduces the absorption of the nutrients, fats and other substances in the chyme.

These and other features of the invention will be more fully understood from the following description of specific embodiments of the invention taken together with the accompanying drawings.

BRIEF DESCRIPTION OF THE DRAWINGS

In the drawings.

Corresponding reference characters indicate corresponding parts throughout the several views of the drawings.

DETAILED DESCRIPTION OF THE INVENTION

Figure 1:
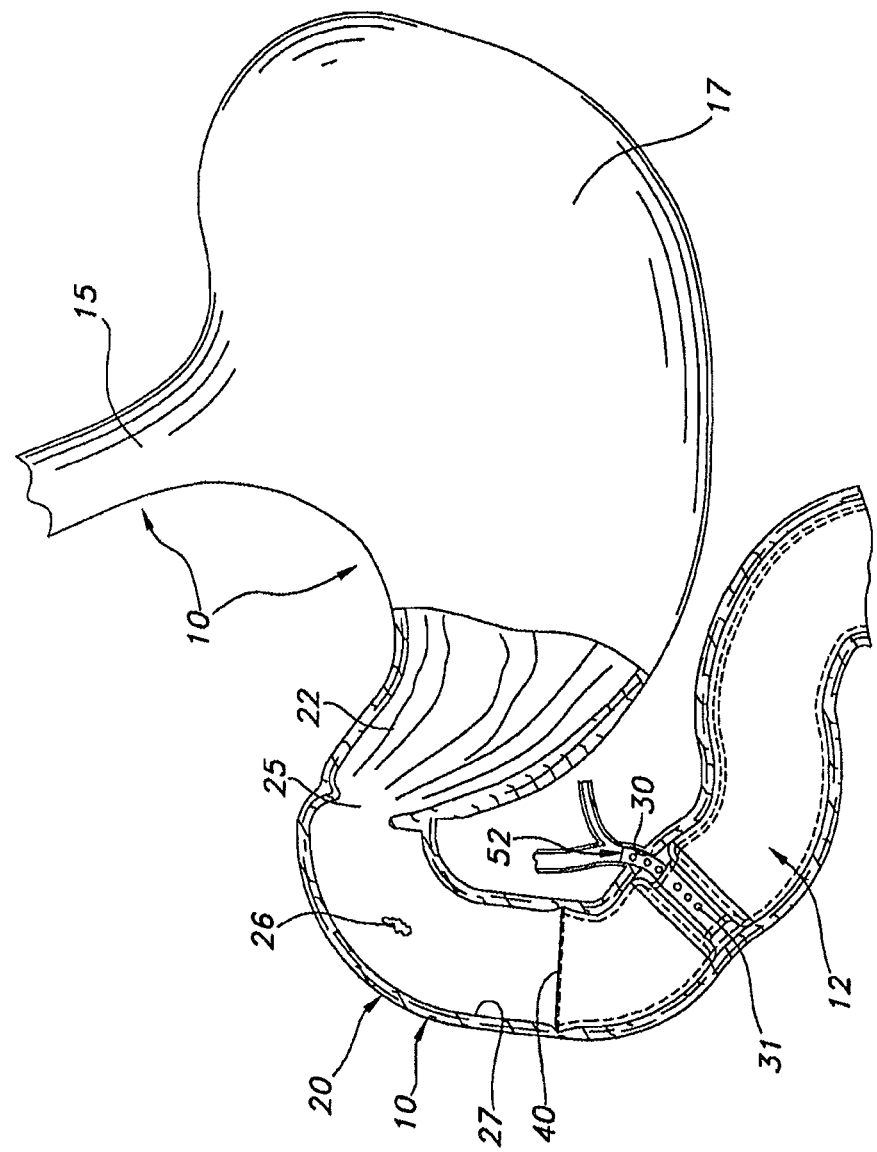
FIG. 1 is an anatomical elevational view of a stomach, duodenum and adjacent portions of the alimentary canal, the wall of the pyloric portion of the stomach and duodenum being broken away to show an anti-obesity stent in accordance with the present invention.

Referring to the drawings and more particularly to FIG. 1, a central portion of the alimentary canal 10 in which the anti-obesity stent 12 is located is illustrated. This portion of the alimentary canal 10 includes the distal segment of the esophagus 15, the stomach 17, and the duodenum 20. The duodenum 20 is the proximate segment of the small intestine. The stomach 17 has a pyloric portion 22 which leads to the duodenum 20 by way of the gastric outlet or pylorus 25. The pylorus 25 forms the distal aperture of the stomach 17 and has an enclosing circular layer of muscle which is normally contracted to close the aperture but which relaxes to provide an open but restrictive passage. Although subject to substantial variation in different individuals, the pylorus 25 has a maximum open diameter of about 2 cm and the duodenum 20 has a diameter which typically is about 18 to 20 mm in a representative patient. The chyme 26 passes from the pyloric portion 22 through the pylorus 25 into the duodenum 20. The duodenum 20 has an inner surface 27 and a papilla of Vater 30 which is a trumpet-mouthed dilatation of the duodenal wall at the opening of the fused bile and pancreatic ducts. Digestive substances, which include digestive fluids 31, are supplied through the papilla of Vater 30, and flow into the interior of the duodenum 20.

Figure 2:
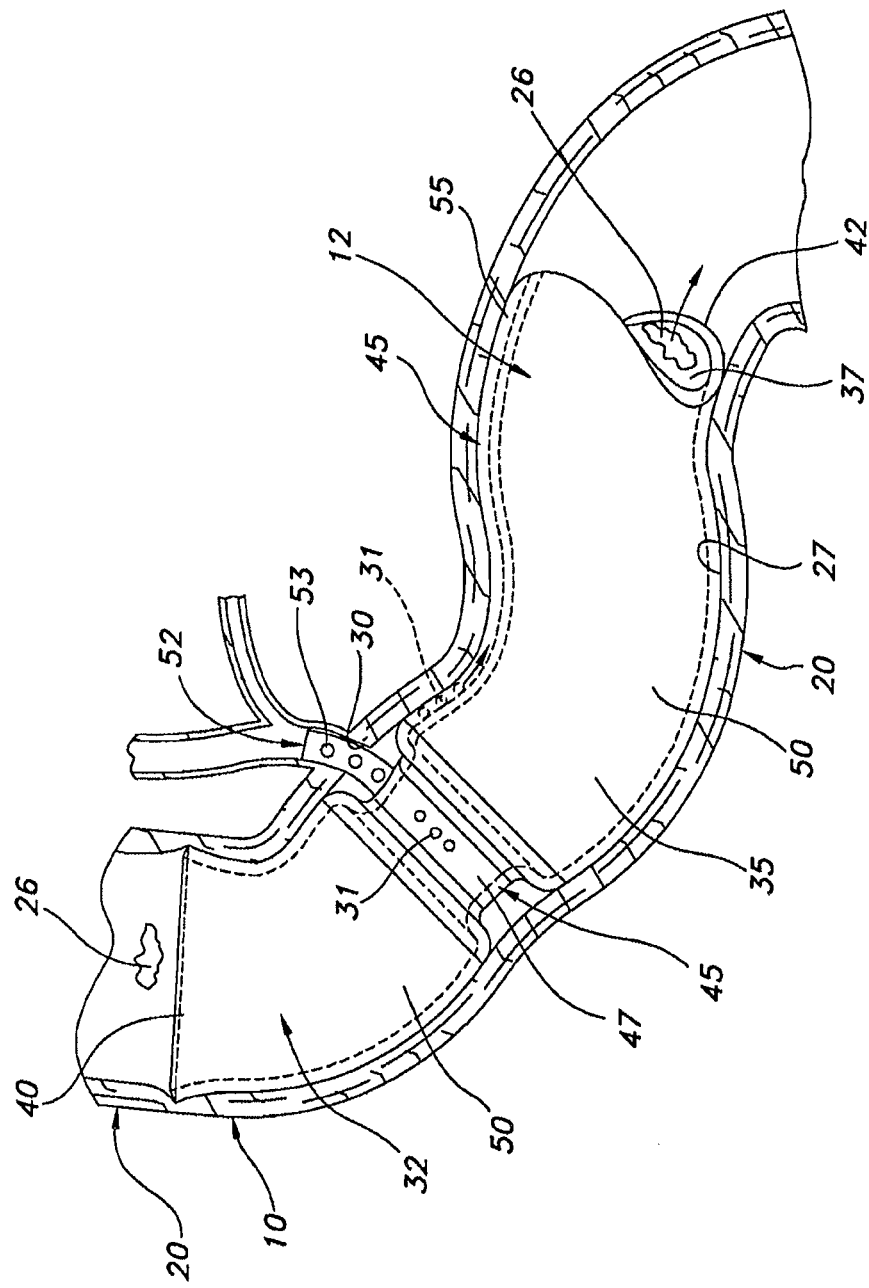
FIG. 2 is an enlarged view of the pyloric portion of the stomach and duodenum in which portions thereof are broken away to show the anti-obesity stent of FIG. 1, the anti-obesity stent being shown as having a substantially straight tubular structure and a transport structure which includes circumferential and axial grooves.

The anti-obesity stent 12 is located within the duodenum 20 as shown in FIG. 1. As shown in FIG. 2, the anti-obesity stent 12 includes a tubular structure 32 which has outer and inner surfaces 35, 37. The tubular structure 32 has proximal and distal ends 40, 42 and is sized to fit within the duodenum 20 in substantially coaxial relation therewith. Preferably, the axial positioning of the tubular structure 32 provides for the distal end 42 to extend to the ligament of Treitz or to an axial position which is distal thereof. The tubular structure 32 typically has an annular cross section. Alternative embodiments of the anti-obesity stent 12 are possible in which the tubular structure 32 has a non-annular cross section, such as elliptical. The tubular structure 32 includes embodiments which extend from the duodenum 20 through the pylorus 25. Such embodiments of the tubular structure 32 may have a safety factor such that the section thereof which extends through the pylorus 25 has an outer diameter which is substantially larger than the opening of the pylorus. Such a safety factor provides for the tubular structure 32 to be retained in the pylorus 25. The tubular structure 32 is impervious or semi-permeable to digestive substances and chyme 26 within the duodenum 20 which partially or completely prevents the chyme within the tubular structure from contacting the inner surface 27 of the duodenum 20 to partially or completely prevent absorption of the nutrients, fats and other substances in the chyme by the portion of the duodenum in which the anti-obesity stent 12 is located. Alternative embodiments of the anti-obesity stent 12 are possible in which the tubular structure 32 is located in sections of the intestine which are axially displaced relative to the duodenum 20. Further alternative gastro-intestinal applications of the anti-obesity stent 12 are possible.

The tubular structure 32 may be formed of expanded polytetrafluoroethylene (ePTFE) or polyurethane. The tubular structure 32 may be formed of biocompatible materials, such as biocompatible polymers including those which are known. Such polymers may include fillers such as metals, carbon fibers, glass fibers or ceramics. Also, such polymers may include olefin polymers, polyethylene, polypropylene, polyvinyl chloride, polytetrafluoroethylene which is not expanded, fluorinated ethylene propylene copolymer, polyvinyl acetate, polystyrene, poly(ethylene terephthalate), naphthalene dicarboxylate derivatives, such as polyethylene naphthalate, polybutylene naphthalate, polytrimethylene naphthalate and trimethylenediol naphthalate, polyurethane, polyurea, silicone rubbers, polyamides, polycarbonates, polyaldehydes, natural rubbers, polyester copolymers, styrene-butadiene copolymers, polyethers, such as fully or partially halogenated polyethers, copolymers, and combinations thereof. Also, polyesters, including polyethylene terephthalate (PET) polyesters, polypropylenes, polyethylenes, polyurethanes, polyolefins, polyvinyls, polymethylacetates, polyamides, naphthalane dicarboxylene derivatives, and natural silk may be included in the tubular structure 32. In alternative embodiments, the tubular structure 32 may be a polymer sleeve.

The tubular structure 32 may be incorporated in a composite structure which also includes a stent structure. The stent structure may include elongate members, such as wires, or a tubular structure having cutouts. The stent structure may be connected to the tubular structure 32 by a seal. The tubular structure 32 may be located within the stent structure in coaxial relation therewith. Such a tubular structure 32 which is within the stent structure may be connected thereto such that the tubular structure is in hanging relation to the stent structure. The connection of the tubular structure 32 to the stent structure may be provided by one or more threads, filaments or similar connectors.

A preferred embodiment of such a tubular structure 32 within a stent structure includes the tubular structure having a diameter which is substantially the same as the diameter of the stent structure. Such a preferred embodiment further includes the end of the tubular structure 32 through which the fluid enters therein being connected to the corresponding end of the stent structure. These ends of the tubular structure 32 and stent structure are typically referred to as the proximal ends. Connection of the proximal ends of the tubular structure 32 and stent structure substantially eliminates any radial clearance between the proximal ends. Such a radial clearance may provide a path for the fluid flow to bypass the lumen of the tubular structure 32. Additional connections of the tubular structure 32 to the stent structure at axial locations which have a distal relation to the proximal ends may be provided.

The connections of the tubular structure 32 to the stent structure within which the tubular structure is located limit radially inward displacement thereof. The outer location of the stent structure relative to the tubular structure 32 limits radially outward displacement thereof.

In a further alternative embodiment, the tubular structure 32 may be located within an outer stent structure and an inner stent structure may be located within the tubular structure 32. Outward radial displacement of the tubular structure 32 is limited by the outer stent structure. Inward radial displacement is limited by the inner stent structure. The connection between the tubular structure 32 and one or more stent structures which are within one another in coaxial relation may provide for the adjacent outer and inner surfaces to be contiguous with one another. Alternatively, the connection may provide for a transverse or radial clearance between the tubular structure 32 and one or more stent structures.

The tubular structure 32 may be a sleeve structure within which is located a stent structure. The sleeve structure 32 may be a PERMALUME® silicone covering for a stent structure constituted by a WALLSTENT® RX Biliary Endoprosthesis, which are made by the Boston Scientific Corporation.

The tubular structure 32 may be a stent structure, such as a WALLSTENT® RX Biliary Endoprosthesis made by the Boston Scientific Corporation. Alternatively, the stent structure may be a NIR® Biliary Stent System made by the Boston Scientific Corporation. Further alternative stent structures are possible.

The stent structure of the tubular structure 32 may be formed of materials such as nitinol, Elgiloy, stainless steel, cobalt chromium, including MP35N, cobalt-based alloy, tantalum, niobium, platinum, gold, titanium, combinations thereof and other biocompatible metals, polymers and materials. Additionally, the stent structure may include structural members which have an inner core formed of tantalum, gold, platinum, iridium, or a combination thereof, and an outer cladding of nitinol to provide composite members for improved radio-opacity or visibility. Examples of such composite members are disclosed in U.S. Patent Application Publication No. 2002/0035396 which is hereby incorporated by reference herein.

The stent structure of the tubular structure 32 may have various embodiments. For example, the stent structure may be self-expanding or expandable by a balloon. The stent structure may include one or more coiled stainless steel springs, helically wound coil springs including a heat-sensitive material, or expanding stainless steel stents formed of stainless steel wire in a zig-zag pattern. The stent structure may be capable of radially contracting or expanding, such as by radial or circumferential distension or deformation. Self-expanding stent structures include stent structures which mechanically urge the stent structure to radially expand, and stent structures which expand at one or more specific temperatures as a result of the memory properties of the stent material for a specific configuration. Nitinol is a material which may be included in the stent structure for providing radial expansion thereof both by mechanical urging, or by the memory properties of the nitinol based on one or more specific temperatures. The stent structure may include one or more of the stent structures disclosed in U.S. Pat. Nos. 4,503,569, 4,733,665, 4,856,516, 4,580,568, 4,732,152, and 4,886,062 which are hereby incorporated by reference herein.

The tubular structure 32 may be treated with anti-thrombogenic agents (such as heparin, heparin derivatives, urokinase, and PPack (dextrophenylalanine proline arginine chloromethylketone)), anti-proliferative agents (such as enoxaprin, angiopeptin, or monoclonal antibodies capable of blocking smooth muscle cell proliferation, hirudin, and acetylsalicylic acid), anti-inflammatory agents (such as dexamethasone, prednisolone, corticosterone, budesonide, estrogen, sulfasalazine, and mesalamine), antineoplastic/antiproliferative/anti-miotic agents (such as paclitaxel, 5-fluorouracil, cisplatin, vinblastine, vincristine, epothilones, endostatin, angiostatin and thymidine kinase inhibitors), anesthetic agents (such as lidocaine, bupivacaine, and ropivacaine), anti-coagulants (such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick anti-platelet peptides), vascular cell growth promotors (such as growth factor inhibitors, growth factor receptor antagonists, transcriptional activators, and translational promotors), vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin), cholesterol-lowering agents, vasodilating agents, and agents which interfere with endogenous vascoactive mechanisms.

Figure 3:
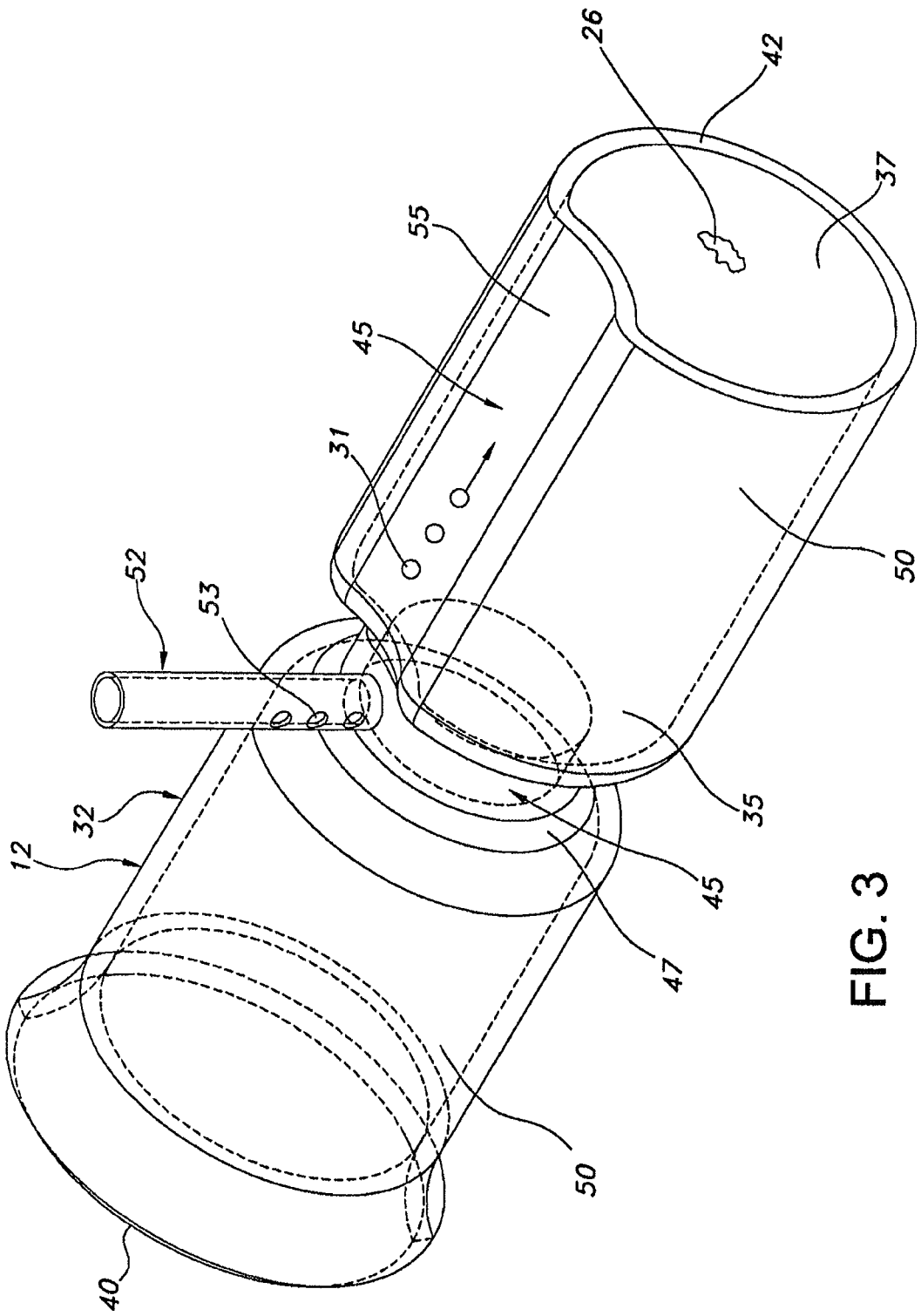
FIG. 3 is a perspective view of the anti-obesity stent of FIG. 2.

The anti-obesity stent 12 has a transport structure 45 at least a part of which is coincident with or connected to the outer surface 35 of the tubular structure 32. One embodiment of the transport structure 45, illustrated in FIGS. 2 and 3, includes a circumferential groove 47 which is formed on the outer surface 35 of the tubular structure 32. The circumferential groove 47 is continuous and transverse relative to the tubular structure 32. The circumferential groove 47 is circular as a result of the tubular structure 32 having an annular cross section, as shown in FIG. 3. The portions of the outer surface 35 which are contiguous with the circumferential groove 47 have respective outer diameters which are greater than the diameter of the inner surface 27 of the duodenum 20 to provide a seal between these portions of the outer surface 35 and the inner surface 27 when the anti-obesity stent 12 is located within the duodenum 20. Such a seal prevents leakage of the digestive fluids 31 within the circumferential groove 47 between the inner and outer surfaces 27, 35.

The portions of the outer surface 35 which are contiguous with the transverse groove 47 have corresponding diameters as a result of the tubular structure 32 having an annular cross section. Alternative embodiments of the tubular structure 32 are possible which have non-annular cross sections.

The transport structure 45, illustrated in FIGS. 2 and 3, includes an elongate axial groove 55 which is formed on the outer surface 35 of the tubular structure 32. The axial groove 55 has an axial orientation relative to the tubular structure 32 and communicates with the circumferential groove 47. The axial groove 55 provides a conduit for the digestive fluids 31 in the circumferential groove 47 to be conveyed to the distal end 42.

The anti-obesity stent 12 has at least one retainer structure 50 which is connected to the outer surface 35 of the tubular structure 32. The retainer structure 50 secures the tubular structure 32 within the duodenum 20 such that the axial position of the circumferential groove 47 is substantially the same as the axial position of the papilla of Vater 30 relative to the duodenum. One embodiment of the retainer structure 50 is the diameter of the outer surface 35 of the tubular structure 32 being sufficiently large to press against the inner surface 27 of the duodenum 20 when the circumferential groove 47 has substantially the same axial position as the papilla of Vater 30. The pressing of the outer surface 35 against the inner surface 27 provides resistance to axial displacement of the tubular structure 32 relative to the duodenum 20.

The anti-obesity stent 12 includes a side tube 52 which is connected to the outer surface 35. The side tube 52 has one end which is connected to the outer surface 35 and one or more perforations 53 adjacent thereto. The side tube 52 has an opposite end which may be inserted through the papilla of Vater 30. The papilla of Vater 30 is part of the duodenum 20 and supplies the digestive fluids 31 thereto. The digestive fluids 31 which are supplied through the papilla of Vater 30 are conveyed through the side tube 52 in a direction which is toward the outer surface 35. When the digestive fluids 31 approach the outer surface 35, the digestive fluids exit the side tube 52 through the perforations 53 and flow into the axial groove 55. Additionally, the insertion of the side tube 52 into the papilla of Vater 30 anchors the side tube therein. This anchoring, in combination with the connection of the side tube 52 to the outer surface 35, substantially fixes the position of the tubular structure 32 within the duodenum 20 by preventing rotational and axial migration of the tubular structure relative to the duodenum.

The digestive fluids 31 which collect in the axial groove 55 flow toward the distal end 42 of the tubular structure 32. Upon reaching the distal end 42, the digestive fluids 31 flow into the duodenum 20. Substantially all of the digestive fluids 31 which flow into the duodenum 20 from the axial groove 55 enter and remain in a portion of the duodenum which has a distal position relative to the distal end 42. Consequently, substantially all of the digestive fluids 31 are partially or completely prevented from entering the interior region of the tubular structure 32. As a result, mixing of the chyme 26 and digestive fluids 31 when the chyme is within the tubular structure 32 is partially or completely prevented.

In an alternative embodiment of the anti-obesity stent 12, the side tube 52 may be secured to a region of the outer surface 35 which is proximal to the distal end 42. Such an embodiment of the side tube 52 extends axially in the distal direction to the distal end 42. The side tube 52 is anchored to the outer surface 35. Consequently, the digestive fluids 31 in the side tube 52 exit therefrom adjacent to the distal end 42. This embodiment of the side tube 52 may include one or more perforations 53 to provide corresponding additional or alternative ports for the digestive fluids 31 to exit the side tube. The digestive fluids 31 which exit the side tube 52 through the perforations 53 may enter the axial grooves 55 and flow therein to the distal end 42. Also, the digestive fluids 31 may enter the axial grooves 55 upon exiting the distal end of an embodiment of the side tube 52 which terminates at a location which is proximal to the distal end 42. Further, an embodiment of the side tube 52 which extends to the distal end 42 and does not include perforations 53 may make unnecessary the axial grooves 55.

In a further alternative embodiment of the anti-obesity stent 12, the side tube 52 may extend through the outer surface 35, and through the wall of the tubular structure 32 between the outer surface and inner surface 37 for attachment to a region of the inner surface 37 which is proximal to the distal end 42. Such an embodiment of the side tube 52 extends axially in the distal direction to the distal end 42. The side tube 52 is anchored to the inner surface 37. Consequently, the digestive fluids 31 in the side tube 52 exit therefrom adjacent to the distal end 42. This embodiment of the side tube 52 may include one or more perforations 53 which would typically be located adjacent to the distal end 42 to provide corresponding additional or alternative ports for the digestive fluids 31 to exit the side tube. The digestive fluids 31 which exit the side tube 52 through the perforations 53 enter the interior of the tubular structure 32 and flow therein to the distal end 42.

In a further alternative embodiment of the anti-obesity stent 12, the side tube 52 may extend through the outer surface 35, and be embedded or buried in the wall of the tubular structure 32 between the outer surface and inner surface 37. This embedding or burying is in an axial portion of the tubular structure 32 which is proximal to the distal end 42. Such an embodiment of the side tube 52 extends axially in the distal direction to the distal end 42. Consequently, the digestive fluids 31 in the side tube 52 exit therefrom adjacent to the distal end 42. This embodiment of the side tube 52 may include one or more perforations 53 which communicate with corresponding apertures in the outer or inner surfaces 35, 37 or both to provide corresponding additional or alternative ports for the digestive fluids 31 to exit the side tube. The digestive fluids 31 which exit the side tube 52 through the perforations 53 and outer surface 35 may enter the axial grooves 55 and flow therein to the distal end 42. Also, the digestive fluids 31 may enter the axial grooves 55 upon exiting the distal end of an embodiment of the side tube 52 which terminates at a location which is proximal to the distal end 42 and communicates with a port in the outer surface 35. Further, an embodiment of the side tube 52 which extends to the distal end 42 and does not include perforations 53 may make unnecessary the axial grooves 55. Also, an embodiment of the side tube 52 which has one or more perforations 53 in communication with corresponding apertures on the inner surface 37 would typically provide for the perforations and apertures to be located adjacent to the distal end 42. The digestive fluids 31 which exit the side tube 52 through the perforations 53 and apertures on the inner surface 37 enter the interior of the tubular structure 32 and flow therein to the distal end 42.

An embodiment of the anti-obesity stent 12 is possible which does not include the side tube 52. Location of this embodiment of the anti-obesity stent 12 within the duodenum 20 provides for the digestive fluids 31, which flow through the papilla of Vater 30 into the interior of the duodenum 20 to collect in the circumferential groove 47. The digestive fluids 31 which collect in the circumferential groove 47 of this embodiment flow into and through the axial groove 55 toward the distal end 42 of the tubular structure 32.

An alternative embodiment of the transport structure 45 includes a conduit which is integral with the tubular structure 32 such that the conduit is between the outer and inner surfaces 35, 37. The digestive fluids 31 in the transport structure 45 are conveyed through the conduit to the distal end 42.

Figure 4:
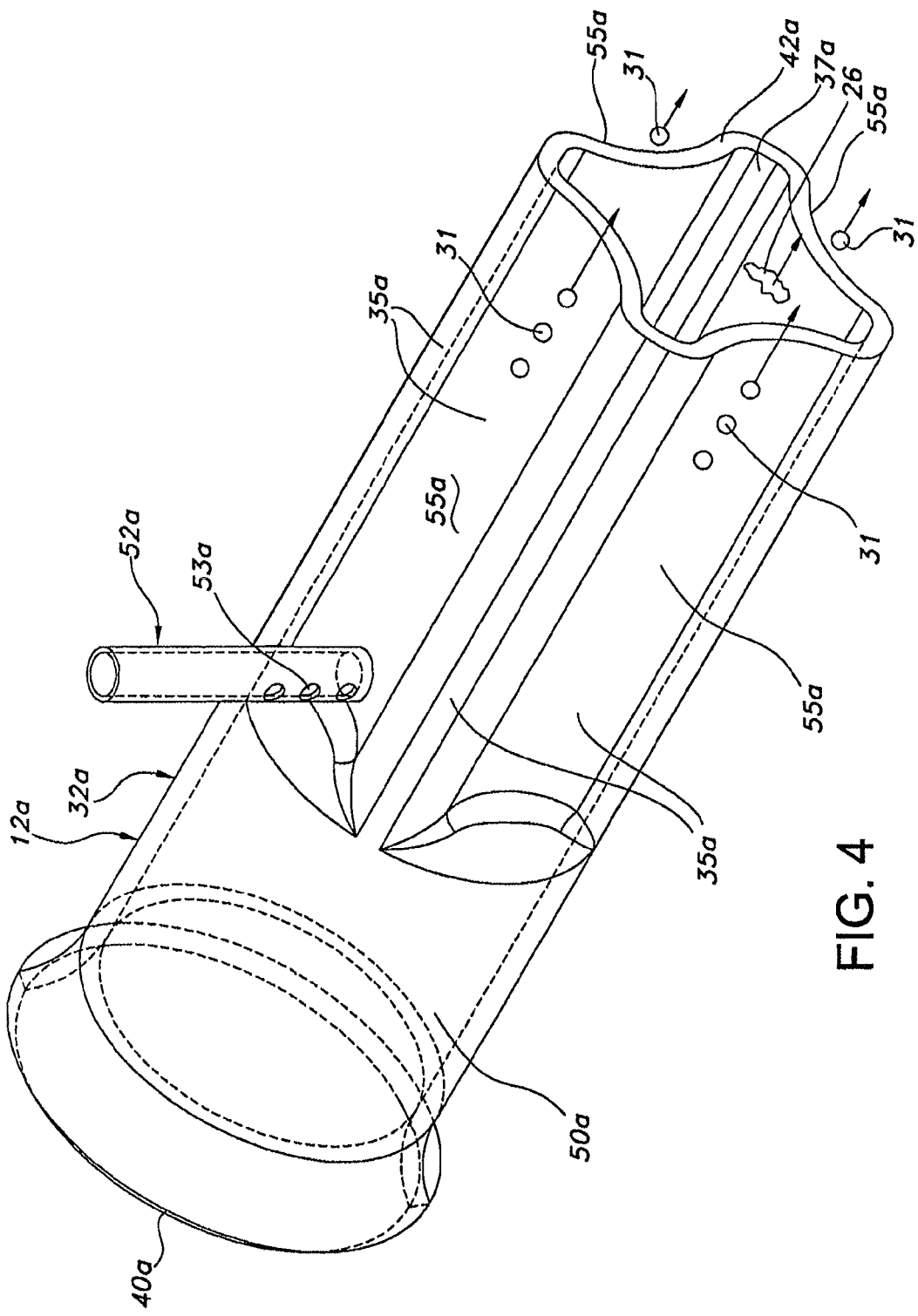
FIG. 4 is a perspective view of an alternative embodiment of the anti-obesity stent of FIG. 1, the anti-obesity stent being shown as having a substantially straight tubular structure and an alternative transport structure.

An alternative embodiment of the anti-obesity stent 12a is shown in FIG. 4. Parts illustrated in FIG. 4 which correspond to parts illustrated in FIGS. 1 to 3 have, in FIG. 4, the same reference numeral as in FIGS. 1 to 3 with the addition of the suffix "a". In this alternative embodiment, the transport structure 45a includes a plurality of axial grooves 55a. The axial grooves 55a provide corresponding conduits for the digestive fluids 31 to be conveyed to the distal end 42a.

Figure 5:
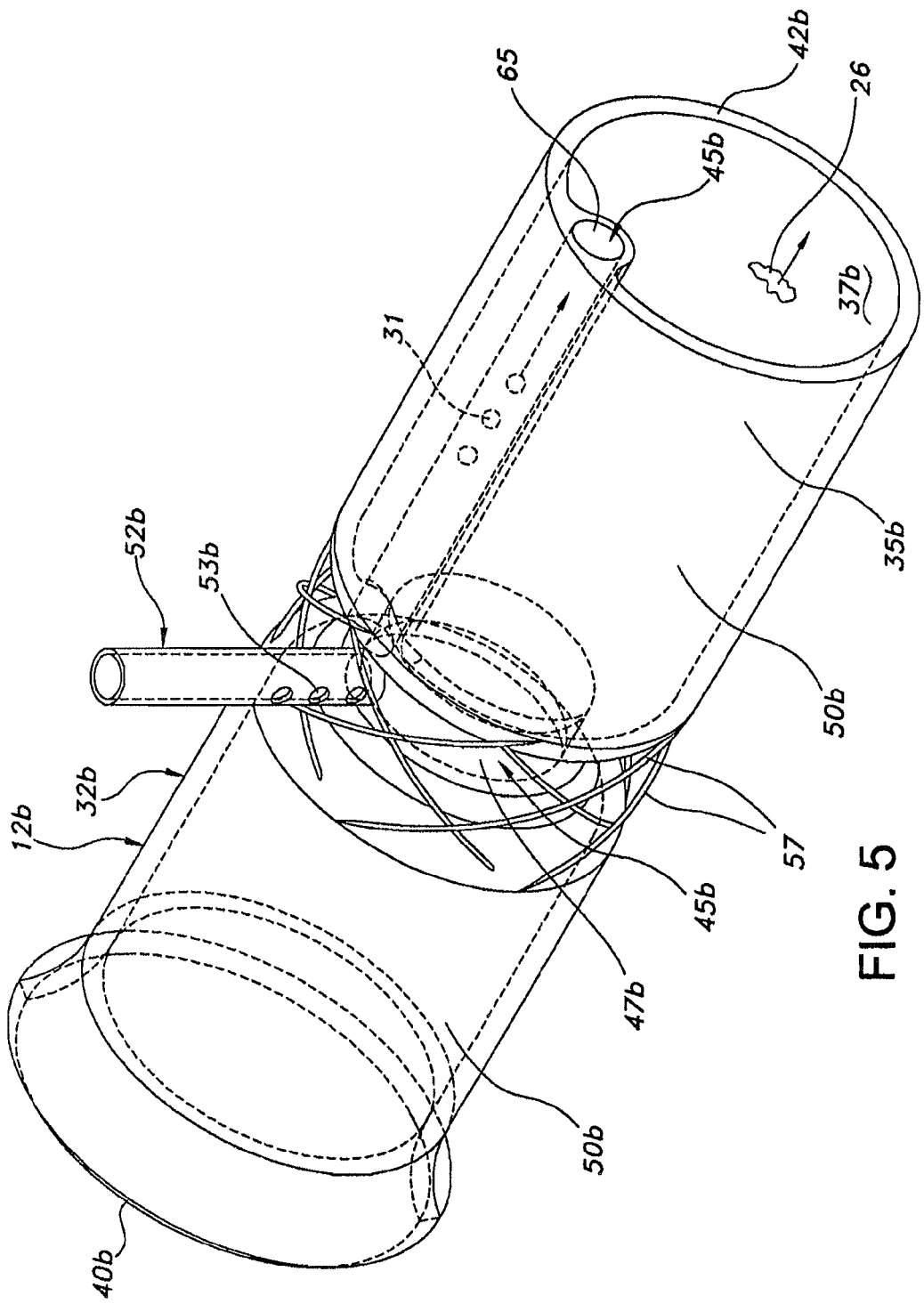
FIG. 5 is a perspective view of a further alternative embodiment of the anti-obesity stent of FIG. 1, the anti-obesity stent being shown as having a substantially straight tubular structure and a further alternative transport structure.

An alternative embodiment of the anti-obesity stent 12b is shown in FIG. 5. Parts illustrated in FIG. 5 which correspond to parts illustrated in FIGS. 1 to 3 have, in FIG. 5, the same reference numeral as in FIGS. 1 to 3 with the addition of the suffix "b". In this alternative embodiment, the transport structure 45b includes a mesh structure 57. The mesh structure 57 is tubular and has a diameter which is larger than a diameter of the transverse groove 47b.

The mesh structure 57 has an annular cross section as a result of the tubular structure 32b having an annular cross section. Alternative embodiments of the mesh structure 57 are possible which have non-annular cross sections.

The mesh structure 57 is attached to the tubular structure 32b in coaxial relation therewith such that the mesh structure covers the circumferential groove 47b to provide a transverse or radial clearance between the inner surface 27 of the duodenum 20 and the circumferential groove. The mesh structure 57 prevents the inner surface 27 of the duodenum 20 from extending into the circumferential groove 47b. Also, the mesh structure 57 prevents the inner surface 27 of the duodenum 20 from contacting the surface of the tubular structure 32b which is within the circumferential groove 47b. Prevention of such contact by the inner surface 27 provides for the passage of the digestive fluids 31 through the papilla of Vater 30 to be unobstructed by the tubular structure 32b. Contact of the inner surface 27 with the tubular structure 32b may obstruct passage and flow of the digestive fluids 31 through the papilla of Vater 30.

The mesh structure 57 shown in FIG. 5 has substantially the same diameter as the diameter of the outer surface 35b of the tubular structure 32b such that the mesh structure is substantially flush with the outer surface 35b. In alternative embodiments, it is possible for the diameter of the mesh structure 57 to be smaller than the diameter of the outer surface 35b provided that the diameter of the mesh structure 57 is larger than the minimum diameter of the transverse groove 47b.

The side tube 52b may be anchored to the tubular structure 32b in various configurations which correspond to the anchoring of the side tube 52 to the tubular structure 32. Alternatively, the side tube 52b may be anchored to the mesh structure 57.

The anti-obesity stent 12b includes an alternative embodiment of the transport structure 45b. The transport structure 52b includes a vent tube 65 which is attached to the inner surface 37b of the tubular structure 32b. The vent tube 65 communicates with the circumferential groove 47b such that the digestive fluids 31 therein are conveyed through the vent tube to the distal end 42b.

Figure 6:
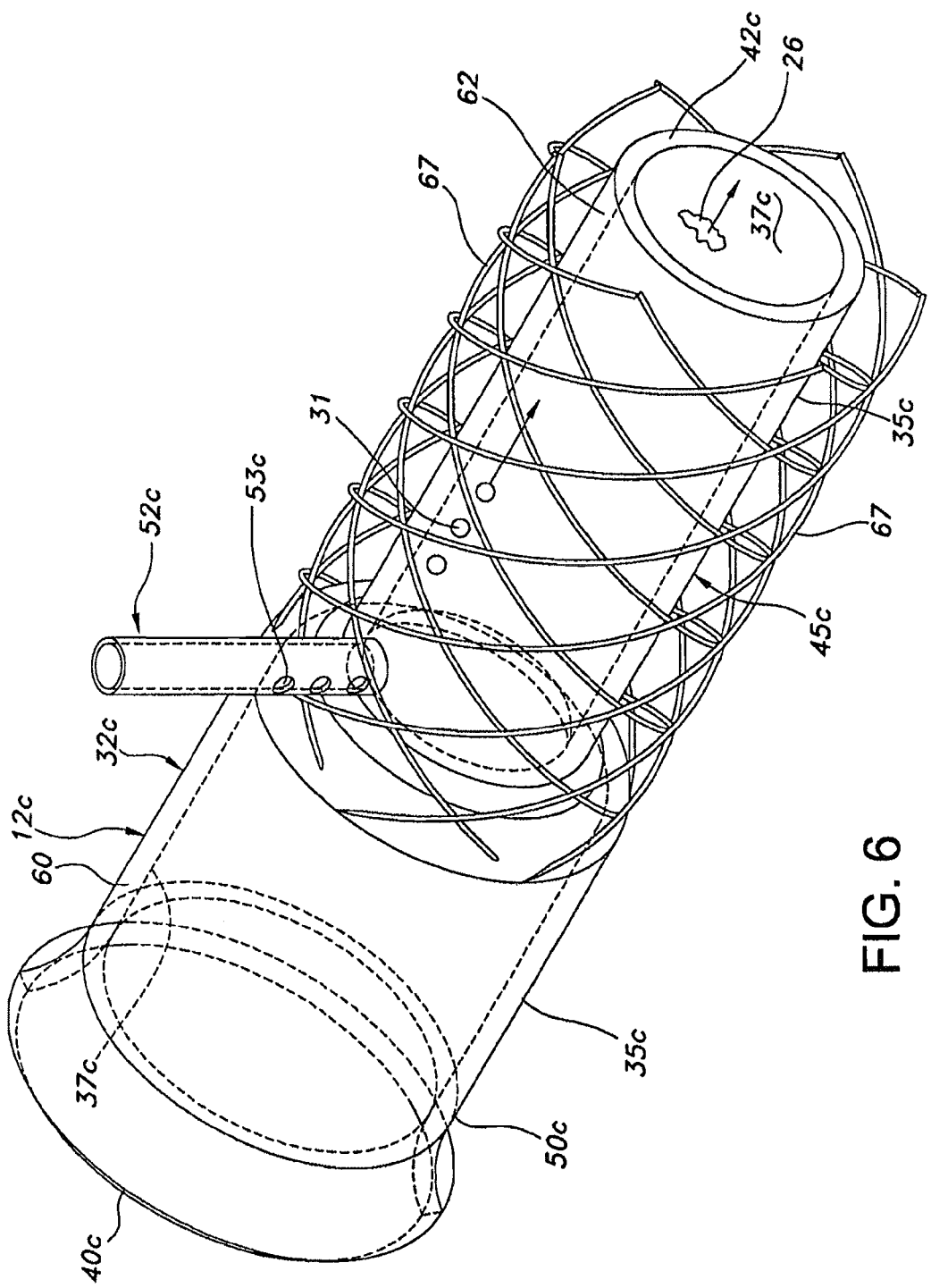
FIG. 6 is a longitudinal cross-sectional view of a further alternative embodiment of the anti-obesity stent of FIG. 1, the anti-obesity stent being shown as having a substantially straight tubular structure which includes proximal and distal portions, the anti-obesity stent being further shown as having a further alternative transport structure.

A further alternative embodiment of the anti-obesity stent 12c is shown in FIG. 6. Parts illustrated in FIG. 6 which correspond to parts illustrated in FIGS. 1 to 3 have, in FIG. 6, the same reference numeral as in FIGS. 1 to 3 with the addition of the suffix "c". The tubular structure 32c has proximal and distal portions 60, 62. The proximal portion 60 has an outer diameter which is larger than the outer diameter of the distal portion 62. The proximal portion 60 has an axial position which is proximal relative to the papilla of Vater 30 when the tubular structure 32c is within the duodenum 20.

The proximal and distal portions 60, 62 have respective annular cross sections. Alternative embodiments of the proximal and distal portions 60, 62 are possible which have non-annular cross sections.

The transport structure 45c includes a mesh structure 67 which is tubular and has an annular cross section. The diameter of the mesh structure 67 is larger than the diameter of the outer surface 35c of the distal portion 62. The mesh structure 67 is attached to the proximal portion 60 in coaxial relation with the distal portion 62. The mesh structure 67 extends between the proximal portion 60 and distal end 42c such that the mesh structure 67 provides a transverse or radial clearance between the inner surface 27 of the duodenum 20 and the outer surface 35c of the distal portion 62. The transverse or radial clearance provides for the passage of the digestive fluids 31 through the papilla of Vater 30 to be unobstructed by the tubular structure 32c. The diameter of the mesh structure 67 is substantially the same as the outer diameter of the proximal portion 60 such that the mesh structure is substantially flush with the outer surface 35c of the proximal portion 60.

The side tube 52c may be anchored to the tubular structure 32c in various configurations which correspond to the anchoring of the side tube 52 to the tubular structure 32. Alternatively, the side tube 52c may be anchored to the mesh structure 67.

Figure 7:
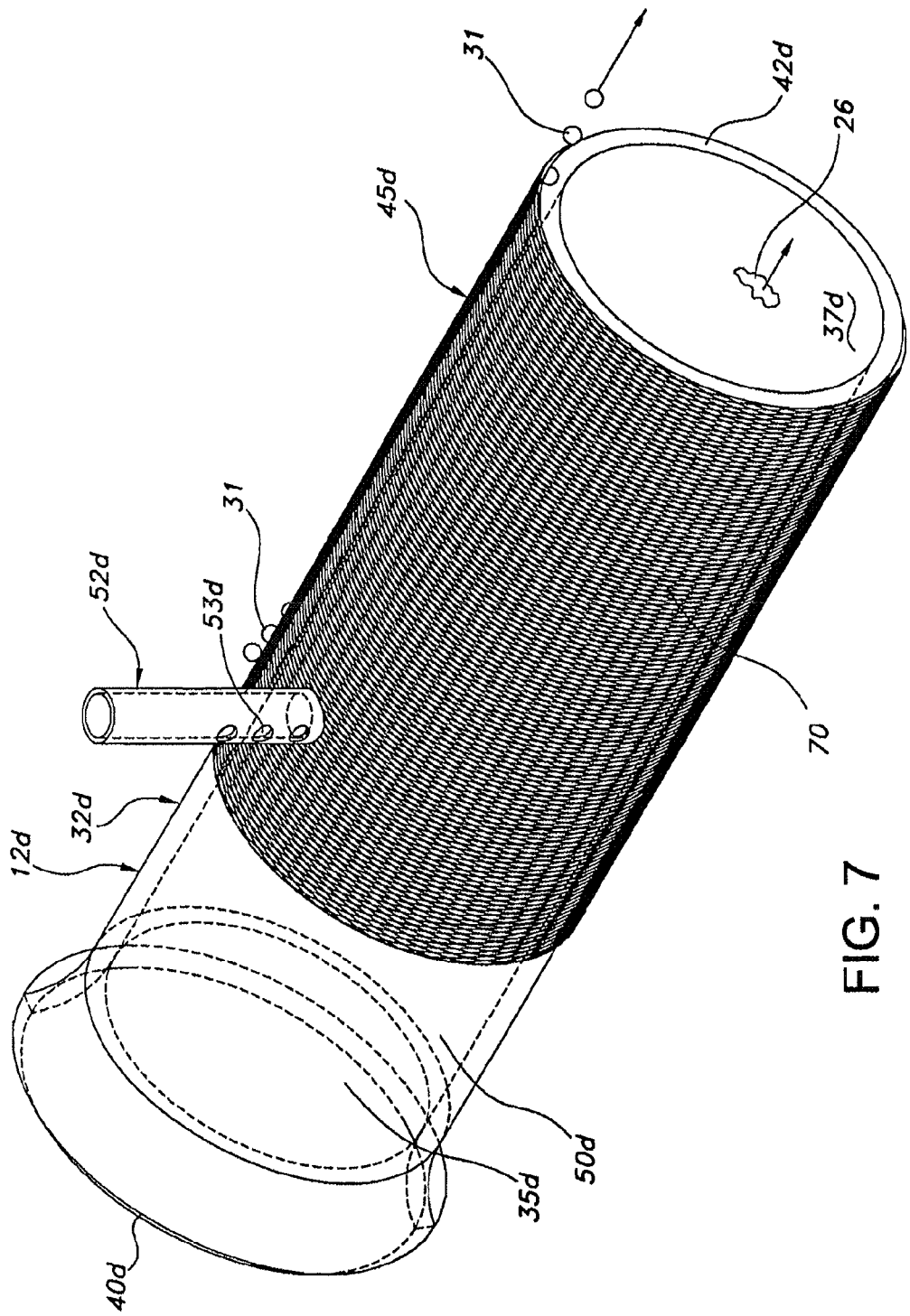
FIG. 7 is a perspective view of a further alternative embodiment of the anti-obesity stent of FIG. 1, the anti-obesity stent being shown as having a substantially straight tubular structure and a further alternative transport structure.

An alternative embodiment of the anti-obesity stent 12d is shown in FIG. 7. Parts illustrated in FIG. 7 which correspond to parts illustrated in FIGS. 1 to 3 have, in FIG. 7, the same reference numeral as in FIGS. 1 to 3 with the addition of the suffix "d". The transport structure 45d includes a wick material 70 which is attached to the outer surface 35d of the tubular structure 32d. The wick material 70 has a structure which may be a mesh or sponge. The wick material 70 has an annular cross section and extends to the distal end 42d. The wick material 70 is formed of polymeric fibers which may be hollow. Alternatively, the wick material 70 may possibly be formed of PTFE. The wick material 70 is in direct contact with the papilla of Vater 30 such that the digestive fluids 31 exiting therefrom are absorbed by the wick material and conveyed through the wick material to the distal end 42d. In alternative embodiments, the digestive fluids 31 in the circumferential grooves 47, 47b may be absorbed by the wick material 70 and conveyed through the wick material to the distal ends 42, 42b.

The side tube 52d may be anchored to the tubular structure 32d in various configurations which correspond to the anchoring of the side tube 52 to the tubular structure 32. When connected to the tubular structure 32d, the side tube 52d may have an axial position which provides for the side tube to be in direct contact with the wick material 70 or, alternatively, for the side tube to have a proximal position relative to the wick material which is axially separated from the wick material.

Figure 8:
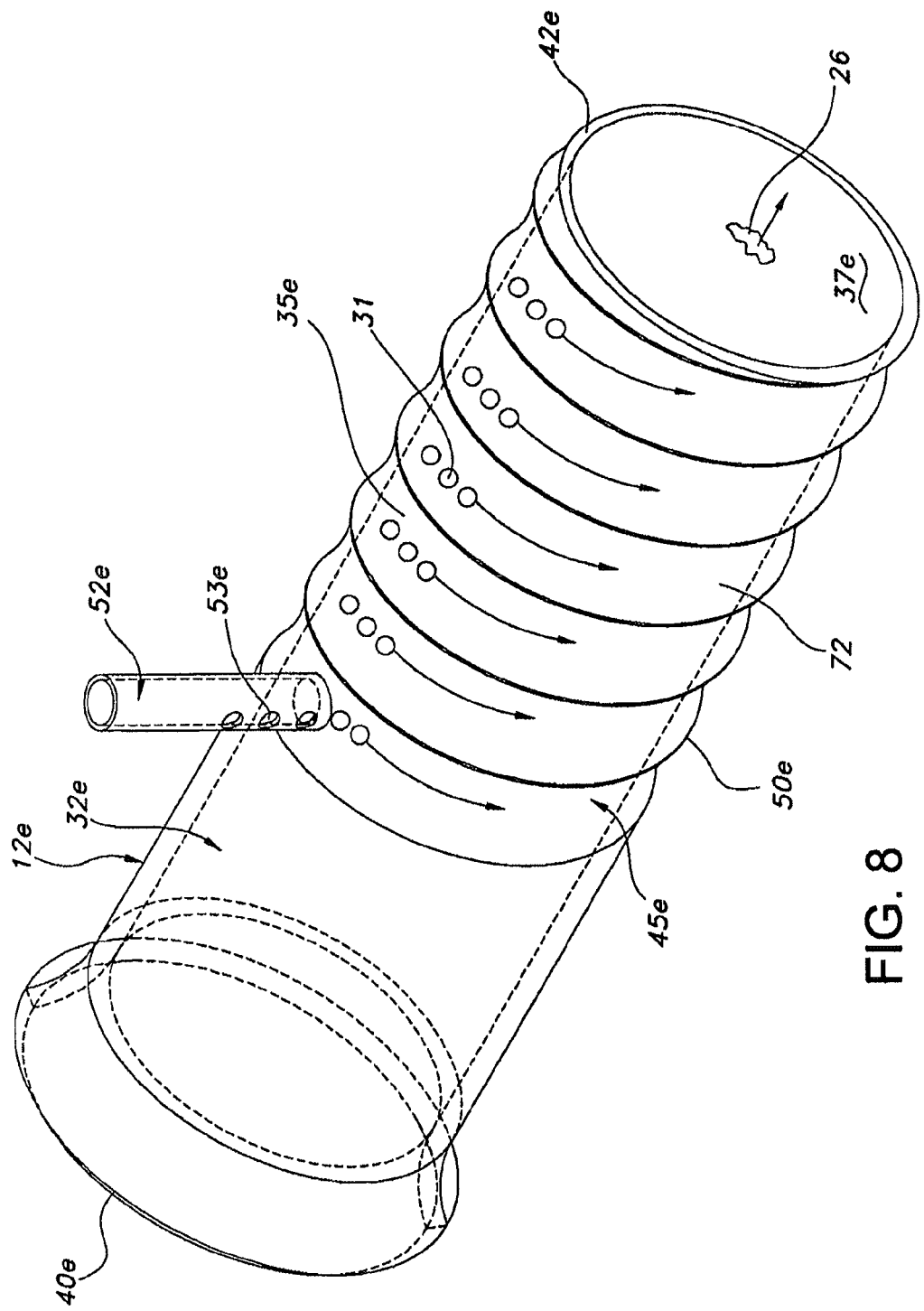
FIG. 8 is a perspective view of a further alternative embodiment of the anti-obesity stent of FIG. 1, the anti-obesity stent being shown as having a substantially straight tubular structure and a further alternative transport structure.

An alternative embodiment of the anti-obesity stent 12d is shown in FIG. 8. Parts illustrated in FIG. 8 which correspond to parts illustrated in FIGS. 1 to 3 have, in FIG. 8, the same reference numeral as in FIGS. 1 to 3 with the addition of suffix "e". The transport structure 45e includes a groove 72 which has rotational and longitudinal orientations which are offset relative to the tubular structure 32e. These offset rotational and longitudinal orientations provide for the groove 72 to be helical in a tubular structure 32e which has an annular cross section, as shown in FIG. 8. The helical groove 72 has a longitudinal axis which substantially coincides with the longitudinal axis of the tubular structure 32e. The helical groove 72 provides a conduit for the digestive fluids 31 to be conveyed to the distal end 42e. This results from locating the anti-obesity stent 12e within the duodenum 20 such that a section of the helical groove, typically one near the proximal end 40e, has the same axial position as the papilla of Vater 30. Consequently, the digestive fluids 31 which flow through the papilla of Vater 30 into the interior of the duodenum 20 land in the helical groove 72. The digestive fluids 31 in the helical groove 72 are displaced toward the distal end 42e by digestive fluids which subsequently flow into the helical groove from the papilla of Vater 30. The digestive fluids 31 remain in the helical groove 72 during this displacement thereof in the distal direction such that the digestive fluids flow around the outer surface 35e in the direction of the helical groove.

The flow of the digestive fluids 31 through the helical groove 72 provides for an increase in the exposure and contact of the digestive fluids 31 with the inner surface 27 of the duodenum 20. This contact between the digestive fluids 31 and the inner surface 27 is further facilitated by providing the outer surface 35e with a diameter which is sufficiently large to limit the transverse or radial clearance between the outer surface 35e and the inner surface 27 of the duodenum. Increasing the contact between the digestive fluids 31 and inner surface 27 contributes to absorption of the digestive fluids by the inner surface 27 of the duodenum 20. Such absorption of the digestive fluids 31 reduces the availability thereof to mix with the chyme 26.

Figure 9:
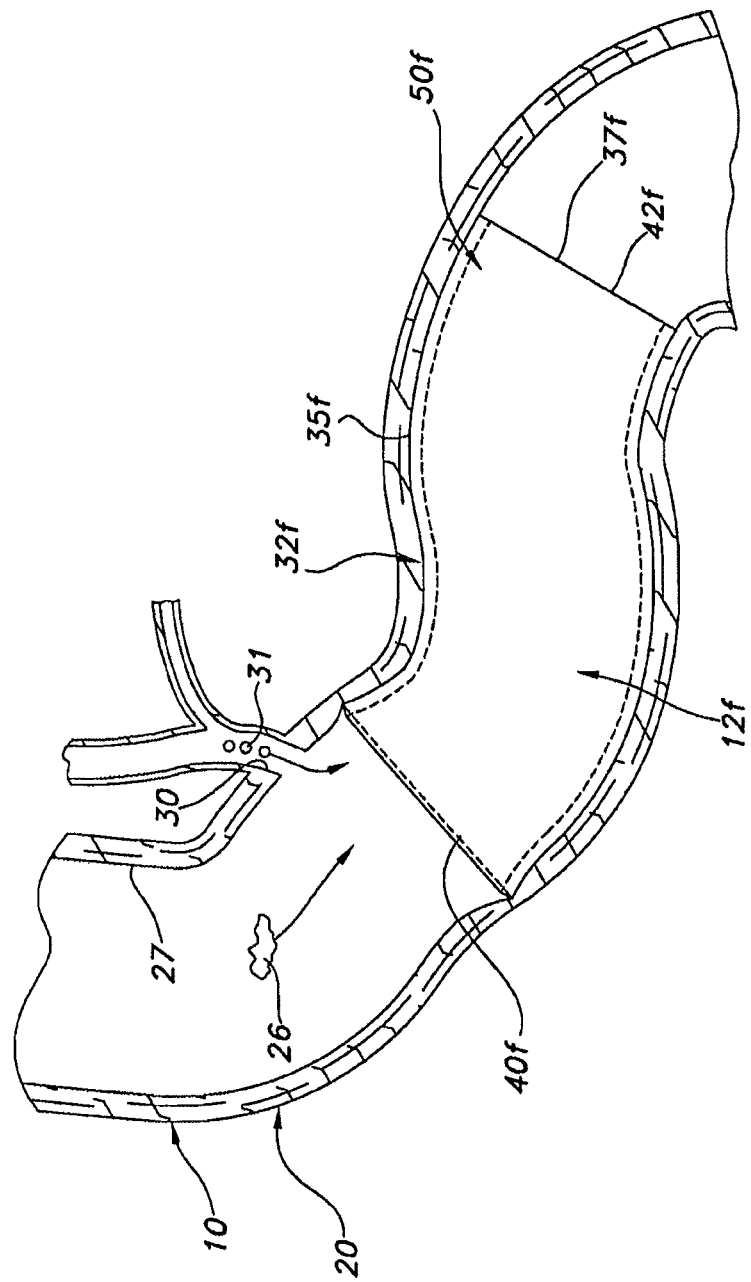
FIG. 9 is a perspective view of a further alternative embodiment of the anti-obesity stent of FIG. 1, the anti-obesity stent being shown as having a substantially straight tubular structure which is distal of the papilla of Vater.

An alternative embodiment of the anti-obesity stent 12f is shown in FIG. 9. Parts illustrated in FIG. 9 which correspond to parts illustrated in FIGS. 1 to 3 have, in FIG. 9, the same reference numeral as in FIGS. 1 to 3 with the addition of the suffix "f". In this alternative embodiment, the tubular structure 32f is sized to fit within the duodenum 20 in substantially coaxial relation therewith. The outer surface 35f has a cross section the shape of which is substantially the same as the shape of the cross section of the inner surface 27 of the duodenum 20. The diameter of the outer surface 35f of the tubular structure 32f is sufficiently large to limit the formation of a radial clearance between the outer surface 35f and inner surface 27 when the tubular structure 32f is located within the duodenum 20. The diameter of the outer surface 35f of the tubular structure 32f may be sufficiently large such that the outer surface 35f engages the inner surface 27 to substantially prevent the formation of a radial clearance between the outer surface 35f and inner surface 27 when the tubular structure 32f is located within the duodenum 20. The tubular structure 32f is impervious or semi-permeable to digestive substances and chyme 26 within the duodenum 20.

The retainer structure 50f, which is connected to the outer surface 35f of the tubular structure 32f, secures the tubular structure 32f within the duodenum 20 such that the proximal end 40f is adjacent to and distal of the papilla of Vater 30. The distal position of the proximal end 40f relative to the papilla of Vater 30 does not prevent the chyme 26 from mixing with the digestive fluids 31 which flow through the papilla of Vater 30 into the interior of the duodenum 20. The chyme 26 and digestive fluids 31 which have an axial position which is proximal relative to the proximal end 40f flow into the interior of the tubular structure 32f through the proximal end 40f. The chyme 26 and digestive fluids 31 continue to flow through the interior of the tubular structure 32f and exit the tubular structure through the distal end 42f.

The limiting of the formation of a radial clearance between the outer surface 35f of the tubular structure 32f and the inner surface 27 of the duodenum 20 limits the flow of the chyme 26 and digestive fluids 31 between the outer surface 35f and the inner surface 27. Consequently, absorption of the nutrients, fats and other substances in the chyme 26 and digestive fluids 31 by the inner surface 27 of the duodenum 20 is limited in the axial portion of the duodenum 20 in which the tubular structure 32f is located. As a result, absorption of the nutrients, fats and other substances in the chyme 26 by the duodenum 20 is reduced.

Figure 10:
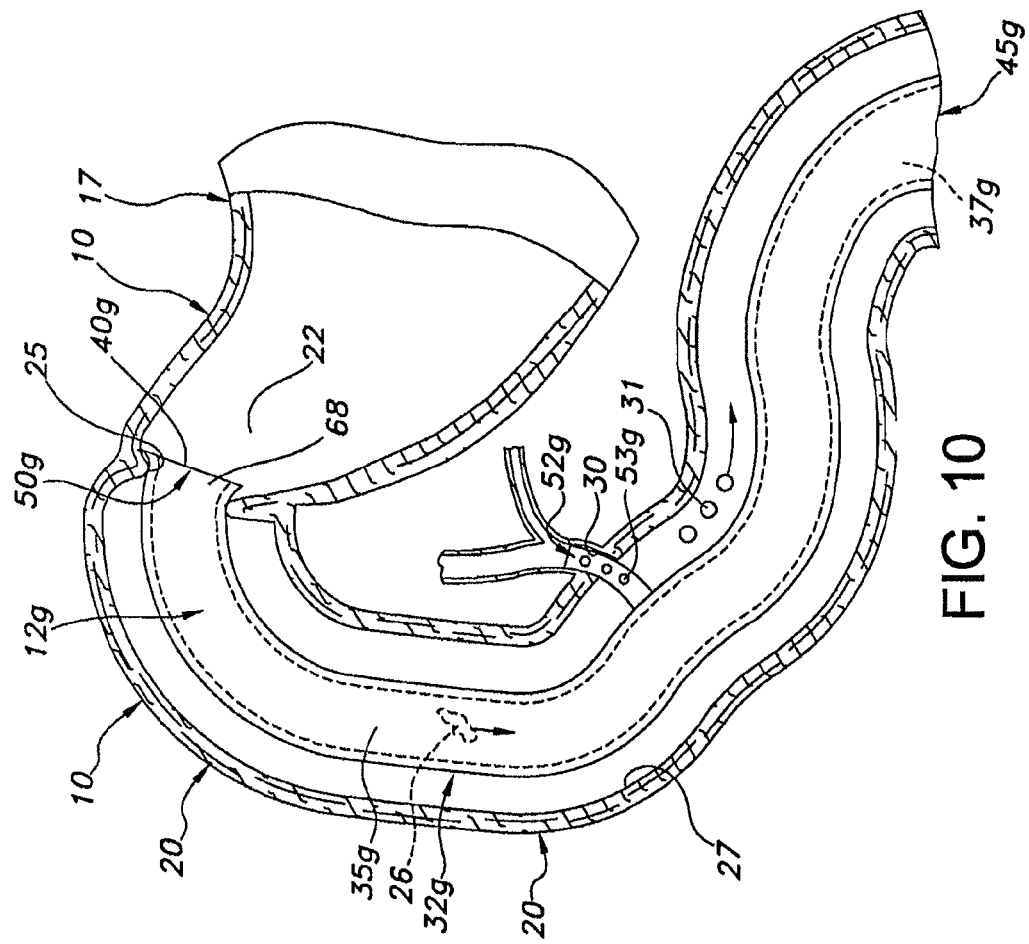
FIG. 10 is a longitudinal cross-sectional view of a further alternative embodiment of the anti-obesity stent of FIG. 1, the anti-obesity stent being shown as having a substantially straight tubular structure and a proximal portion which is outwardly flared.

An alternative embodiment of the anti-obesity stent 12g is shown in FIG. 10. Parts illustrated in FIG. 10 which correspond to parts illustrated in FIGS. 1 to 3 have, in FIG. 10, the same reference numeral as in FIGS. 1 to 3 with the addition of the suffix "g". The retainer structure 50g includes a proximal portion 68 of the tubular structure 32g which is axial and contains the proximal end 40g, as shown in FIG. 10. The proximal portion 68 has an axial position which is proximal relative to the transport structure 45g. The proximal portion 68 is separated axially from the transport structure 45g a sufficient distance such that the proximal portion 68 extends through the pylorus 25 when the transport structure 45g is positioned to receive the digestive fluids 31 from the papilla of Vater 30. The extension of the proximal portion 68 through the pylorus 25 provides for the chyme 26 to enter the tubular structure 32g in the pyloric portion 22 of the stomach 17. Consequently, the chyme 26 is within the tubular structure 32g when the chyme enters the duodenum 20. This obstructs the chyme 26 from being absorbed by the inner surface 27 or mixing with the digestive fluids 31 in the duodenum 20 which are upstream of the distal end 42g.

The proximal portion 68 is outwardly flared such that the proximal end 40g and an adjoining part of the proximal portion 68 which extends through the pylorus 25 has an outer diameter which is larger than an outer diameter of an intermediate portion of the tubular structure 32g. The outward flaring of the proximal portion 68 provides resistance to axial displacement of the tubular structure 32g in a distal direction relative to the duodenum 20. The proximal portion 68 and intermediate portion of the tubular structure 32g have annular cross sections as a result of the tubular structure 32g having an annular cross section. The retainer structure 50g may be incorporated into alternative embodiments of the anti-obesity stent, such as the anti-obesity stents 12, 12a, 12b, 12c, 12d, 12e.

The proximal portion 68 of the tubular structure 32g has an outer diameter which is sufficiently large to press against the inner surface of the pylorus 25 such that resistance to axial displacement of the tubular structure 32g relative to the duodenum 20 is provided. The proximal portion 68 has an annular cross section. The retainer structure 50g may further include a circumferential groove formed on the outer surface of the proximal portion 68 which extends through the pylorus 25. This circumferential groove is located axially relative to the proximal portion 68 such that the inner surface of the pylorus 25 extends into the circumferential groove such that resistance to axial displacement of the tubular structure 32g relative to the duodenum 20 is provided. The circumferential groove is transverse relative to the proximal portion 68, and may be circular.

Figure 11:
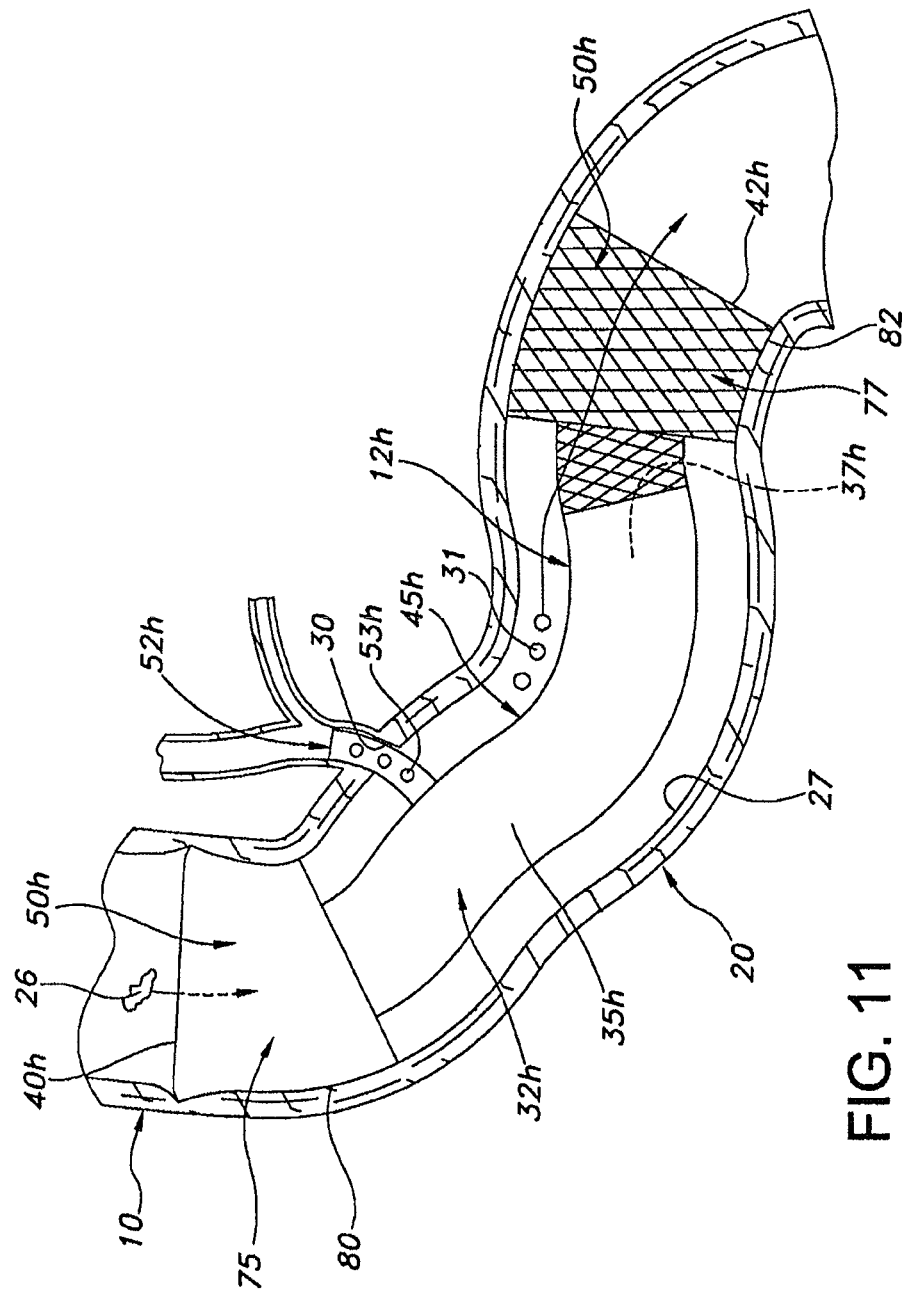
FIG. 11 is a longitudinal cross-sectional view of a further alternative embodiment of the anti-obesity stent of FIG. 1, the anti-obesity stent being shown as having a substantially straight tubular structure and proximal and distal anchors.

An alternative embodiment of the anti-obesity stent 12h is shown in FIG. 11. Parts illustrated in FIG. 11 which correspond to parts illustrated in FIGS. 1 to 3 have, in FIG. 11, the same reference numeral as in FIGS. 1 to 3 with the addition of the suffix "h". In this alternative embodiment, the retainer structure 50h includes a proximal anchor 75 which is tubular and has an inner surface which is connected to the outer surface 35h of the tubular structure 32h. The proximal anchor 75 is located adjacent to the proximal end 40h. The retainer structure 50h further includes a distal anchor 77 which is tubular and has an inner surface which is connected to the outer surface 35h. The distal anchor 77 is located adjacent to the distal end 42h.

The proximal and distal anchors 75, 77 are transversely expandable to outer diameters which are sufficiently large such that corresponding outer surfaces 80, 82 of the proximal and distal anchors engage the inner surface 27 of the duodenum 20. This engagement substantially prevents the formation of a radial clearance between the outer surfaces 80, 82 and the inner surface 27 when the tubular structure 32h is located within the duodenum 20 such that the papilla of Vater 30 is axially positioned between the proximal and distal anchors 75, 77. The axial positioning of proximal and distal anchors 75, 77 relative to the papilla of Vater 30 allows the digestive fluids 31 which flow through the papilla of Vater into the duodenum 20 to become contained between the tubular structure 32h and the inner surface 27. The distal anchor 77 or a distal portion of the tubular structure 32h or both are permeable to the digestive fluids 31 contained between the tubular structure 32h and the inner surface 27 of the duodenum 20.

Figure 12:
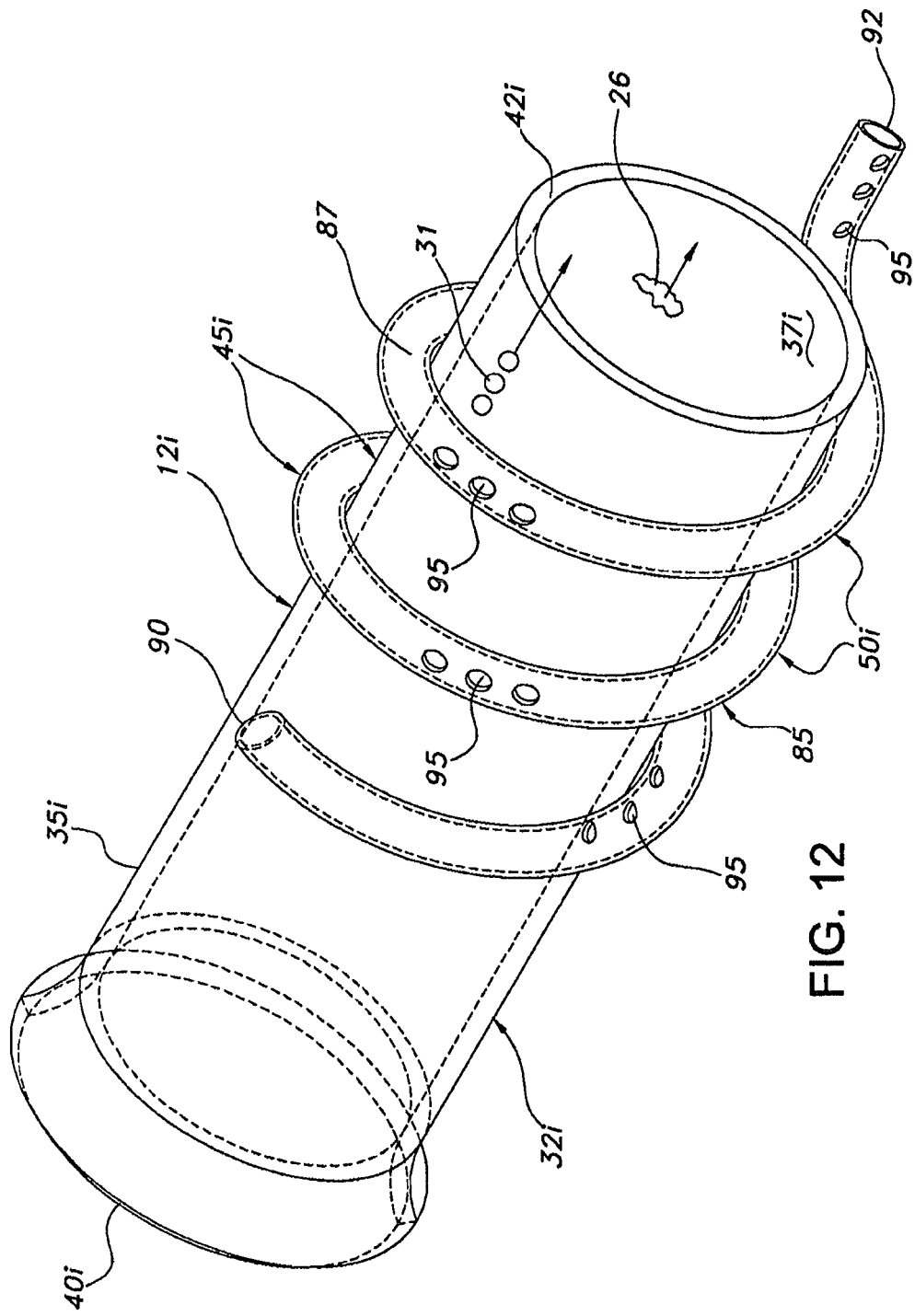
FIG. 12 is a perspective view of a further alternative embodiment of the anti-obesity stent of FIG. 1, the anti-obesity stent being shown as having a substantially straight tubular structure and a further alternative transport structure.

An alternative embodiment of the anti-obesity stent 12i is shown in FIG. 12. Parts illustrated in FIG. 12 which correspond to parts illustrated in FIGS. 1 to 3 have, in FIG. 12, the same reference numeral as in FIGS. 1 to 3 with the addition of the suffix "i". In this alternative embodiment, the transport structure 45i includes an elongate support member 85 which is secured to the outer surface 35i of the tubular structure 32i. The support member 85 has rotational and longitudinal orientations which are offset relative to the tubular structure 32i. These offset rotational and longitudinal orientations provide for the support member 85 to be helical in a tubular structure 32i which has an annular cross section, as shown in FIG. 12. The support member 85 has a longitudinal axis which substantially coincides with the longitudinal axis of the tubular structure 32i. The support member 85 contacts the inner surface 27 of the duodenum 20 and provides a transverse or radial clearance between the inner surface 27 and the outer surface 35i of the tubular structure 32i. The transverse or radial clearance provides for the separation of the tubular structure 32i from the papilla of Vater 30 to facilitate the flow of the digestive fluids 31 out of the papilla of Vater 30.

The support member 85 includes a tubular structure 87 having proximal and distal ends 90, 92 which are open. The digestive fluids 31 may flow through the proximal end 90 into the lumen of the tubular structure 87. The digestive fluids 31 are carried through the lumen to the distal end 90.

The support member 85 has perforations 95 in the tubular structure 87. The perforations 95 provide for the digestive fluids 31 to flow into the lumen of the tubular structure 87. The digestive fluids 31 which flow into the lumen are carried therein in the distal direction and may exit therefrom through the distal end 92.

An alternative embodiment of the support member 85 is possible in which the proximal end 90 is closed such that the perforations 95 provide for the entry of the digestive fluids 31 into the lumen of the tubular structure 87. A further alternative embodiment of the support member 85 is possible which does not have the perforations 95 such that the opening in the proximal end 90 provides for the entry of the digestive fluids 31 into the lumen of the tubular structure 87. A further alternative embodiment of the support member 85 is possible in which the tubular structure 87 does not have a lumen such that the digestive fluids 31 flow in the transverse or radial clearance between the inner surface 27 of the duodenum 20 and the outer surface 35i of the tubular structure 32i toward the distal end 42i.

The securing of the support member 85 to the outer surface 35i fixes the support member thereto. The contact between the support member 85 and inner surface 27 provides resistance to displacement of the support member 85 relative to the inner surface 27. Consequently, the support member 85 provides the retainer structure 50i.

In a further alternative embodiment, the support member 85 may include at least three longitudinal support members which are secured to the outer surface 35i as an alternative to the helical support member shown in FIG. 12. The longitudinal support members have longitudinal orientations relative to the tubular structure 32i. The longitudinal support members are spaced equidistant from one another circumferentially relative to the outer surface 35i. The longitudinal support members provide a transverse or radial clearance between the inner and outer surfaces 27, 35i.

The longitudinal support members each include a tubular structure having proximal and distal ends which are open. The digestive fluids 31 may flow through the proximal ends into the lumen of the tubular structures of the longitudinal support members. The digestive fluids 31 are carried through the lumens to the distal ends of the longitudinal support members.

The longitudinal support members have perforations in the corresponding tubular structures thereof. The perforations provide for the digestive fluids 31 to flow into the lumens of the tubular structures. The digestive fluids 31 which flow into the lumens are carried therein in the distal direction and may exit therefrom through the distal ends.

An alternative embodiment of the longitudinal support members is possible in which the corresponding proximal ends are closed such that the perforations provide for the entry of the digestive fluids 31 into the lumens of the tubular structures. A further alternative embodiment of the longitudinal support members is possible which does not have the perforations such that the open proximal ends provide for the entry of the digestive fluids 31 into the lumens of the tubular structures. A further alternative embodiment of the longitudinal support members is possible in which the tubular structures do not have corresponding lumens such that the digestive fluids 31 flow in the transverse or radial clearance between the inner surface 27 of the duodenum 20 and the outer surface of the tubular structure toward the distal end thereof.

The securing of the longitudinal support members to the outer surface of the tubular structure fixes the support members thereto. The contact between the longitudinal support members and inner surface 27 provides resistance to displacement of the support members relative to the inner surface 27. Consequently, the longitudinal support members provide the retainer structure.

Alternative embodiments of the anti-obesity stent 12, 12a, 12b, 12c, 12d, 12e, 12f, 12g, 12h, 12i have respective retainer structures 50, 50a, 50b, 50c, 50d, 50e, 50f, 50g, 50h which include a circumferential groove formed on the outer surface 35, 35a, 35b, 35c, 35d, 35e, 35f, 35g, 35h such that the inner surface 27 of the duodenum 20 extends into the circumferential groove to provide resistance to axial displacement of the tubular structure 32, 32a, 32b, 32c, 32d, 32e, 32f, 32g, 32h relative to the duodenum 20. Such a circumferential groove is transverse relative to the tubular structure 32, 32a, 32b, 32c, 32d, 32e, 32f, 32g, 32h and may be circular.

Further alternative embodiments of the anti-obesity stent 12, 12a, 12b, 12c, 12d, 12e, 12f, 12g, 12h have respective retainer structures 50, 50a, 50b, 50c, 50d, 50e, 50f, 50g, 50h which include a protuberance extending from the outer surface 35, 35a, 35b, 35c, 35d, 35e, 35f, 35g, 35h of the tubular structure 32, 32a, 32b, 32c, 32d, 32e, 32f, 32g. The protuberance has an outer surface and a radial dimension such that the outer surface of the protuberance engages the inner surface 27 of the duodenum 20 when the tubular structure 32, 32a, 32b, 32c, 32d, 32e, 32f, 32g, 32h, 32i is located within the duodenum 20 and the axial position of the transport structure 45, 45a 45b, 45c, 45d, 45e, 45f, 45g, 45h, 45i is positioned to receive the digestive fluids 31 from the papilla of Vater 30. The engagement of the protuberance with the inner surface 27 of the duodenum 20 provides resistance to axial displacement of the tubular structure 32, 32a, 32b, 32c, 32d, 32e, 32f, 32g, 32h, 32i relative to the duodenum 20. The protuberance may include hooks and pins which have a distal end which is pointed and may include one or more barbs. The protuberance may engage the inner surface 27 to provide the resistance to axial displacement of the tubular structure 32, 32a, 32b, 32c, 32d, 32e, 32f, 32g, 32h, 32i for the tubular structures having outer surfaces 35, 35a, 35b, 35c, 35d, 35e, 35f, 35g, 35h, 35i with various diameters. Such outer surfaces 35, 35a, 35b, 35c, 35d, 35e, 35f, 35g, 35h, 35i may have a diameter which is smaller than the diameter of the inner surface 27 or, alternatively, may have a diameter which is larger than the diameter of the inner surface 27. The tubular structures 32, 32a, 32b, 32c, 32d, 32e, 32f, 32g, 32h, 32i may have an annular cross section such that the outer surfaces 35, 35a, 35b, 35c, 35d, 35e, 35f, 35g, 35h, 35i are circular.

Further alternative embodiments of the anti-obesity stents 12, 12a, 12b, 12c, 12d, 12e, 12f, 12g, 12h have respective retainer structures 50, 50a, 50b, 50c, 50d, 50e, 50f, 50g, 50h which include one or more sections of the outer surface 35, 35a, 35b, 35c, 35d, 35e, 35f, 35g, 35h being roughened or knurled. Such outer surfaces 35, 35a, 35b, 35c, 35d, 35e, 35f, 35g, 35h have a diameter which is substantially the same as or larger than the diameter of the inner surface 27. The tubular structures 32, 32a, 32b, 32c, 32d, 32e, 32f, 32g, 32h may have an annular cross section such that the outer surfaces 35, 35a, 35b, 35c, 35d, 35e, 35f, 35g, 35h are circular.

Further alternative embodiments of the anti-obesity stent 12, 12a, 12b, 12c, 12d, 12e, 12f, 12g, 12h have respective retainer structures 50, 50a, 50b, 50c, 50d, 50e, 50f, 50g, 50h which include a semi-rigid band secured to the tubular structure 32, 32a, 32b, 32c, 32d, 32e, 32f, 32g, 32h. The semi-rigid band is arcuate or circular, and has a transverse orientation relative to the tubular structure 32, 32a, 32b, 32c, 32d, 32e, 32f, 32g, 32h. The semi-rigid band is transversely expandable to one or more outer diameters which are sufficiently large to anchor the tubular structure 32, 32a, 32b, 32c, 32d, 32e, 32f, 32g, 32h to the inner surface 27 of the duodenum 20. The semi-rigid band may have a ratcheting mechanism which provides for the transverse expansion of the band. The semi-rigid band may include polymeric material or metal.

Further alternative embodiments of the anti-obesity stent 12, 12a, 12b, 12c, 12d, 12e, 12f, 12g, 12h have respective retainer structures 50, 50a, 50b, 50c, 50d, 50e, 50f, 50g, 50h which include a collapsible ring structure which is secured to the tubular structure 32, 32a, 32b, 32c, 32d, 32e, 32f, 32g, 32h. Such a collapsible ring structure may improve the opening and retention of the tubular structure 32, 32a, 32b, 32c, 32d, 32e, 32f, 32g, 32h within the duodenum 20.

Further alternative embodiments of the anti-obesity stents 12, 12a, 12b, 12c, 12d, 12e, 12f, 12g, 12h, 12i have respective retainer structures 50, 50a, 50b, 50c, 50d, 50e, 50f, 50g, 50h, 50i which include one or more elongate anchor members which are secured to the tubular structure 32, 32a, 32b, 32c, 32d, 32e, 32f, 32g, 32h, 32i. Each anchor member is arcuate, and has a transverse orientation relative to the tubular structure 32, 32a, 32b, 32c, 32d, 32e, 32f, 32g, 32h, 32i. The arcuate extent of the anchor members may be 300 degrees. The anchor members extend radially outward from the outer surfaces 35, 35a, 35b, 35c, 35d, 35e, 35f, 35g, 35h, 35i a sufficient distance to anchor the tubular structure 32, 32a, 32b, 32c, 32d, 32e, 32f, 32g, 32h, 32i to the inner surface 27 of the duodenum 20. The arcuate configuration of the one or more anchor members provides corresponding circumferential gaps between the ends of each arcuate member. The circumferential gaps provide increased radial clearances in the locations thereof in the region between the outer surfaces 35, 35a, 35b, 35c, 35d, 35e, 35f, 35g, 35h, 35i and the inner surface 27 which facilitates the axial flow of the digestive fluids 31 through the region.

Further alternative embodiments of the anti-obesity stent 12, 12a, 12b, 12c, 12d, 12e, 12f, 12g, 12h have respective retainer structures 50, 50a, 50b, 50c, 50d, 50e, 50f, 50g, 50h which include sutures. Such sutures anchor the outer surface 35, 35a, 35b, 35c, 35d, 35e, 35f, 35g, 35h of the tubular structure 32, 32a, 32b, 32c, 32d, 32e, 32f, 32g, 32h to the inner surface 27 of the duodenum 20 and, in some embodiments, to the stomach 17. The sutures prevent axial and rotational displacement of the anti-obesity stents 12, 12a, 12b, 12c, 12d, 12e, 12f, 12g, 12h relative to the duodenum 20 and stomach 17.

Further alternative embodiments of the anti-obesity stents 12, 12a, 12b, 12c, 12d, 12e, 12f, 12g, 12h have respective retainer structures 50, 50a, 50b, 50c, 50d, 50e, 50f, 50g, 50h which include an adhesive material which bonds the outer surface 35, 35a, 35b, 35c, 35d, 35e, 35f, 35g, 35h and inner surface 27 to one another. Such outer surfaces 35, 35a, 35b, 35c, 35d, 35e, 35f, 35g, 35h have a diameter which is substantially the same as or larger than the diameter of the inner surface 27. The tubular structures 32, 32a, 32b, 32c, 32d, 32e, 32f, 32g, 32h may have an annular cross section such that the outer surfaces 35, 35a, 35b, 35c, 35d, 35e, 35f, 35g, 35h are circular. A further alternative embodiment of the anti-obesity stent 12i has a retainer structure 50i which includes an adhesive material which bonds the outer surface of the support member 85 and inner surface 27 to one another.

Further alternative embodiments of the anti-obesity stents 12, 12a, 12b, 12c, 12d, 12e, 12f, 12g, 12h have respective retainer structures 50, 50a, 50b, 50c, 50d, 50e, 50f, 50g, 50h which induce cells, such as are present on the inner surface 27 of the duodenum 20, to grow into the outer surfaces 35, 35a, 35b, 35c, 35d, 35e, 35f, 35g, 35h of the tubular structures 32, 32a, 32b, 32c, 32d, 32e, 32f, 32g, 32h. A further alternative embodiment of the anti-obesity stent 12i has a retainer structure 50i which induces cells, such as are present on the inner surface 27 of the duodenum 20, to grow into the outer surface of the support member 85.

Further alternative embodiments of the anti-obesity stents 12, 12a, 12b, 12c, 12d, 12e, 12f, 12g, 12h have respective retainer structures 50, 50a, 50b, 50c, 50d, 50e, 50f, 50g, 50h which include a balloon or sponge located within the tubular structures 32, 32a, 32b, 32c, 32d, 32e, 32f, 32g, 32h. Such a balloon and sponge expands after the tubular structure 32, 32a, 32b, 32c, 32d, 32e, 32f, 32g, 32h is positioned in the duodenum 20. The expansion of the balloon and sponge results in radial expansion of the tubular structures 32, 32a, 32b, 32c, 32d, 32e, 32f, 32g, 32h to cause engagement of the outer surfaces 35, 35a, 35b, 35c, 35d, 35e, 35f, 35g, 35h with the inner surface 27 which anchors the tubular structure within the duodenum 20.

Alternative embodiments of the anti-obesity stent 12, 12a, 12b, 12c, 12d, 12e, 12f, 12g, 12h, 12i provide for different embodiments of the transport structures 45, 45a, 45b, 45c, 45d, 45e, 45f, 45g, 45h, 45i to be used in combination with one another such that the digestive fluids 31 therein are conveyed through the respective transport structures to the distal end 42, 42a, 42b, 42c, 42d, 42e, 42f, 42g, 42h, 42i. Such combinations of the transport structures 45, 45a, 45b, 45c, 45d, 45e, 45f, 45g, 45h, 45i provide for one of the transport structures to constitute a proximal transport structure which is in direct communication with the papilla of Vater 30. Another of the transport structures is contiguous with the distal end 42, 42a, 42b, 42c, 42d, 42e, 42f, 42g, 42h, 42i. The proximal and distal transport structures may be directly connected to one another to provide a conduit for conveying the digestive fluids 31 from the papilla of Vater 30 to the distal end 42, 42a, 42b, 42c, 42d, 42e, 42f, 42g, 42h, 42i. In further alternative embodiments, additional transport structures may be connected between the proximal and distal transport structures to provide a conduit for conveying the digestive fluids 31, sequentially through the respective transport structures, from the papilla of Vater 30 to the distal end 42, 42a, 42b, 42c, 42d, 42e, 42f, 42g, 42h, 42i.

An anti-obesity stent, such as the anti-obesity stent 12, 12a, 12b, 12c, 12d, 12e, 12f, 12g, 12h, 12i, may be used according to a method for inducing weight loss in a patient. The method includes inserting a tubular structure of the anti-obesity stent into a duodenum, such as the duodenum 20, in substantially coaxial relation therewith. The tubular structure has outer and inner surfaces and proximal and distal ends. Embodiments of the tubular structure to which this inserting may be applied include the tubular structures 32, 32a, 32b, 32c, 32d, 32e, 32f, 32g, 32h, 32i. The anti-obesity stent has a transport structure at least a part of which is connected to the outer surface of the tubular structure. The transport structure extends to the distal end.

The method further includes locating the tubular structure within and axially relative to the duodenum such that the transport structure is positioned to receive digestive fluids from a papilla of Vater, such as the papilla of Vater 30, on an inner surface of the duodenum. Embodiments of the transport structure to which this locating may be applied are the transport structures 45, 45a, 45b, 45c, 45d, 45e, 45f, 45g, 45h, 45i. The locating further positions the anti-obesity stent such that the distal end of the tubular structure has a distal position relative to the papilla of Vater. Embodiments of the distal end of the tubular structure to which this locating may be applied include the distal ends 42, 42a, 42b, 42c, 42d, 42e, 42f, 42g, 42h, 42i.

The method further includes engaging a retainer structure of the anti-obesity stent with the inner surface of the duodenum to secure the transport structure in the position thereof to receive digestive fluids from the papilla of Vater. Embodiments of the retainer structure to which this engaging may be applied include the retainer structures 50, 50a, 50b, 50c, 50d, 50e, 50f, 50g, 50h, 50i.

The method for inducing weight loss in a patient may provide for the use of an anti-obesity stent in which the transport structure thereof has a groove which is formed on the outer surface. Such anti-obesity stents are shown in FIGS. 1 to 5, and 8, and include grooves 47, 55a, 47b, 72. In this embodiment of the method, the locating of the tubular structure includes positioning the groove such that a section thereof has circumferential and axial positions which are substantially the same as the circumferential and axial positions of the papilla of Vater within the duodenum. The engaging of the retainer structure includes engaging the retainer structure with the inner surface of the duodenum to secure the section of the groove in the circumferential and axial positions thereof which are substantially the same as the circumferential and axial positions of the papilla of Vater.

The method for inducing weight loss in a patient may provide for the use of an anti-obesity stent in which the transport structure thereof has a circumferential groove which is formed on the outer surface. Such a circumferential groove is continuous, and transverse relative to the tubular structure. Such anti-obesity stents are shown in FIGS. 1 to 3 and 5, and include circumferential grooves 47, 47b. In this embodiment of the method, the locating of the tubular structure includes positioning the circumferential groove such that an axial position thereof is substantially the same as the axial position of the papilla of Vater when the tubular structure is secured within the duodenum by the retainer structure. The engaging of the retainer structure includes engaging the retainer structure with the inner surface of the duodenum to secure the circumferential groove in the axial position thereof which is substantially the same as the axial position of the papilla of Vater.

U.S. Pat. No. 6,740,121 is hereby incorporated by reference herein. The following U.S. Patent Applications are hereby incorporated by reference herein:

Title: Anti-Obesity Dual Stent; Inventors: Katie Krueger, William Bertolino, Barry Weitzner, and Claude Clerc; Filed on same date as present U.S. patent application Ser. No. 11/443,402;

Title: Anti-Obesity Diverter Structure; Inventors: Katie Krueger, and Harold W. Martins; Filed on same date as present U.S. patent application Ser. No. 11/443,516; and Title: Anti-Obesity Flow Controller; Inventor: Barry Weitzner; Filed on same date as present U.S. patent application Ser. No. 11/443,544.

While the invention has been described by reference to certain preferred embodiments, it should be understood that numerous changes could be made within the spirit and scope of the inventive concept described. Accordingly, it is intended that the invention not be limited to the disclosed embodiments, but that it have the full scope permitted by the language of the following claims.

What is claimed is:

1. An anti-obesity device, comprising:
    an elongated tubular structure having a first channel extending therethrough from a first end to a second end along a longitudinal axis, the tubular structure being insertable into a duodenum;
    a side tube extending away from the outer wall of the tubular structure and having a second channel extending therethrough, the side tube being formed so that, when the first end of the tubular structure is positioned adjacent the pylorus, the side tube is positioned adjacent a papilla of vater, the side tube including a plurality of perforations formed in an outer wall thereof; and
    a pathway formed along the outer wall of the tubular structure and extending from the side tube to guide digestive fluids from the perforations distally through the duodenum.

2. The anti-obesity device of claim 1, further comprising a circumferential groove formed on an outer wall of the tubular structure and extending transverse to the longitudinal axis, a diameter of the circumferential groove being smaller than a diameter of outlying portions of the tubular structure.

3. The anti-obesity device of claim 2, wherein the side tube is positioned in the circumferential groove.

4. The anti-obesity device of claim 1, wherein the pathway is defined by a reduced diameter length of the tubular structure.

5. The anti-obesity device of claim 1, wherein the pathway is a groove following a helical path relative to the longitudinal axis of the tubular structure.

6. The anti-obesity device of claim 1, wherein the pathway is formed as a depressed portion of the outer wall of the tubular structure.

7. The anti-obesity device of claim 1, wherein the pathway is formed as a vent tube housed within the outer wall.

8. The anti-obesity device of claim 1, further comprising a mesh structure extending over the outer surface of the tubular structure.

9. The anti-obesity device of claim 1, wherein the pathway extends to the second end of the tubular structure.

10. The anti-obesity device of claim 1, wherein the tubular structure is formed of one of polytetrafluoroethylene, polyurethane and a biocompatible polymer.

11. The anti-obesity device of claim 1, further comprising a retaining arrangement formed at the first end of the tubular structure to contact a pylorus, the retaining arrangement maintaining an axial position of the first end such that the tubular structure extends into the duodenum and the side tube is positioned adjacent the papilla of vater.

12. The anti-obesity device of claim 1, further comprising additional fluid pathways positioned on the outer surface of the tubular structure and positioned equidistant from one another along the outer surface, the pathways extending parallel to the longitudinal surface.

13. An anti-obesity device, comprising:
    an elongated tubular structure extending from a first end to a second end to a second end and including a first channel extending therethrough; and
    a side tube formed on an outer wall of the tubular structure and having a plurality of perforations formed therein, the perforations being open to a second channel extending through the side tube, wherein the side tube is separated from the first end of the tubular structure by a distance selected such that when a retainer formed on the first end of the tubular structure is positioned adjacent to a pylorus, a free end of the side tube is received within a papilla of vater.

14. The anti-obesity device of claim 13, wherein the side tube is helically wound over the outer surface of the tubular structure and extends to the second end.

15. The anti-obesity device of claim 13, wherein the side tube extends radially away from the outer surface of the tubular structure.

16. The anti-obesity device of claim 13, further comprising a fluid pathway extending from the side tube to the second end of the tubular structure to guide a flow of digestive fluids therethrough from the papilla of vater toward the second end.

17. The anti-obesity device of claim 13, further comprising a plurality of fluid pathways extending from the side tube to the second end of the tubular structure, the fluid pathways being formed as a plurality of axial grooves.

18. The anti-obesity device of claim 13, further comprising a circumferential groove formed on an outer wall of the tubular structure and extending transverse to the longitudinal axis, a diameter of the circumferential groove being smaller than a diameter of outlying portions of the tubular structure.

19. A method for inducing weight loss, comprising:
    inserting into a duodenum an elongated tubular structure having a first channel extending therethrough from a first end to a second end along a longitudinal axis, the tubular structure further comprising a fluid pathway formed along an outer wall thereof and extending from a side tube of the tubular structure; and
    aligning a side tube connected to an outer wall of the tubular structure with a papilla of vater such that the side tube extends away from the outer surface and into the papilla of Vater, the side tube including a plurality of perforations formed in an outer wall thereof to guide digestive fluids into the fluid pathway to guide a flow of digestive fluids distally from the perforations toward the second end of the tubular structure.

20. The method of claim 19, further comprising the step of engaging a retainer with a pylorus to secure an axial position of the tubular structure within the duodenum.

* * * * *